United States Patent
Brennan et al.

(10) Patent No.: US 11,904,020 B2
(45) Date of Patent: Feb. 20, 2024

(54) BICYCLIC PEPTIDE LIGANDS SPECIFIC FOR TREM2

(71) Applicant: Bicycle Tx Limited, Cambridge (GB)

(72) Inventors: Paul Brennan, Cambridge (GB); Amy Brown, Cambridge (GB); Liuhong Chen, Cambridge (GB); John Davis, Cambridge (GB); Yuliya Demydchuk, Cambridge (GB); Donatella Di Rienzo, Cambridge (GB); Ellen Gowans, Cambridge (GB); Rama McCrory, Cambridge (GB); Emma Mead, Cambridge (GB); Emma Murphy, Cambridge (GB); Mike Rigby, Cambridge (GB); Michael Skynner, Cambridge (GB); Tom Smith, Cambridge (GB); Steven Stanway, Cambridge (GB)

(73) Assignee: BicycleTx Limited, Cambridge (GB)

( * ) Notice: Subject to any disclaimer, the term of this patent is extended or adjusted under 35 U.S.C. 154(b) by 0 days.

(21) Appl. No.: 17/698,185

(22) Filed: Mar. 18, 2022

(65) Prior Publication Data
US 2022/0296726 A1    Sep. 22, 2022

(30) Foreign Application Priority Data

Mar. 19, 2021 (GB) .................................. 2103870
Oct. 14, 2021 (GB) .................................. 2114729

(51) Int. Cl.
*A61K 47/64* (2017.01)
*A61K 47/54* (2017.01)
*C07K 14/00* (2006.01)

(52) U.S. Cl.
CPC ............ *A61K 47/64* (2017.08); *A61K 47/545* (2017.08); *C07K 14/001* (2013.01)

(58) Field of Classification Search
None
See application file for complete search history.

(56) References Cited

PUBLICATIONS

Chen et al. Bicyclic Peptide Ligands Pulled out of Cysteine-Rich Peptide Libraries. J. Am. Chem. Soc. 2013, 135, 6562-6569. (Year: 2013).*

* cited by examiner

*Primary Examiner* — Aradhana Sasan
*Assistant Examiner* — Jia-Hai Lee
(74) *Attorney, Agent, or Firm* — Morgan, Lewis & Bockius LLP

(57) ABSTRACT

The present invention relates to polypeptides which are covalently bound to molecular scaffolds such that two or more peptide loops are subtended between attachment points to the scaffold. In particular, the invention describes peptides which bind to TREM2. The invention also relates to multimeric binding complexes which comprise at least two of said bicyclic peptide ligands. The invention also includes pharmaceutical compositions comprising said peptide ligands and multimeric binding complexes and the use of said peptide ligands, multimeric binding complexes and pharmaceutical compositions in preventing, suppressing or treating a disease or disorder mediated by TREM2.

12 Claims, 4 Drawing Sheets
Specification includes a Sequence Listing.

A

B

C
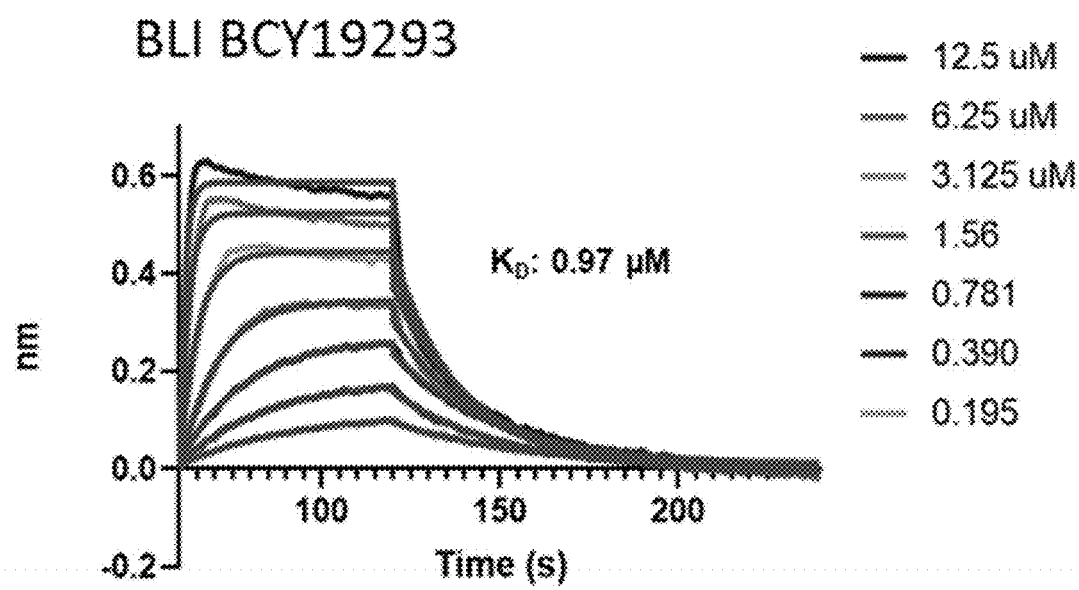
D
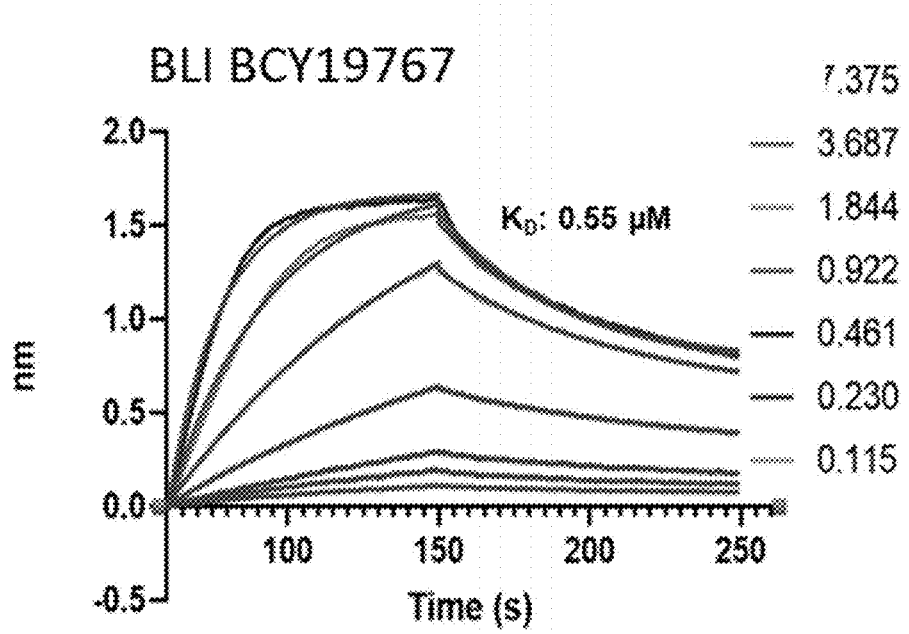
FIGURE 1 (ctd)

A

B

C
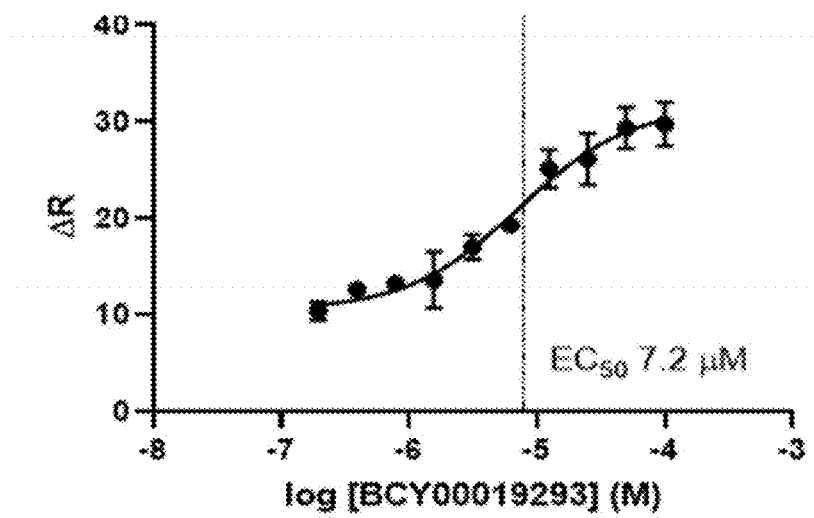
D
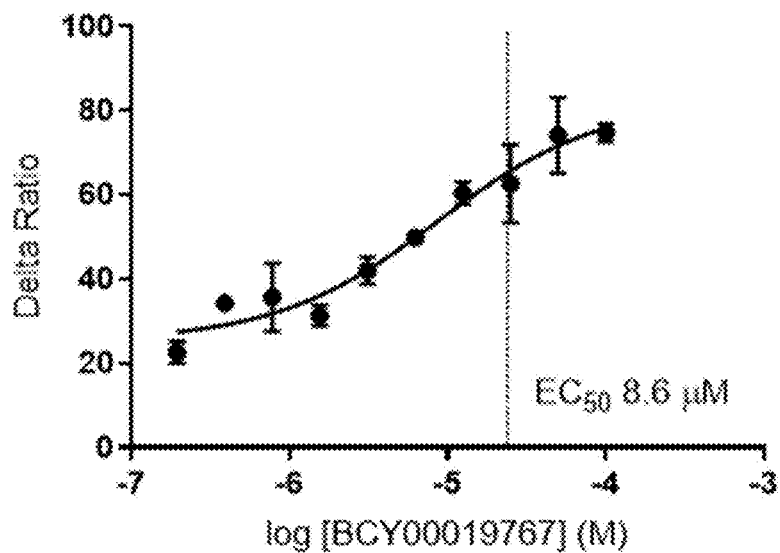
FIGURE 2 (ctd)

BICYCLIC PEPTIDE LIGANDS SPECIFIC FOR TREM2

CROSS-REFERENCE TO RELATED APPLICATIONS

This application claims priority to, and the benefit of, Great Britain Application No. 2103870.8, filed on Mar. 19, 2021, and Great Britain Application No. 2114729.3, filed on Oct. 14, 2021. The entire contents of which are hereby incorporated by reference herein in their entireties.

SEQUENCE LISTING

A computer readable text file, entitled "SequenceListing.txt" created on or about Mar. 18, 2022 with a file size of about 25,047 bytes contains the sequence listing for this application and is hereby incorporated by reference in its entirety.

FIELD OF THE INVENTION

The present invention relates to polypeptides which are covalently bound to molecular scaffolds such that two or more peptide loops are subtended between attachment points to the scaffold. In particular, the invention describes peptides which bind to TREM2. The invention also relates to multimeric binding complexes which comprise at least two of said bicyclic peptide ligands. The invention also includes pharmaceutical compositions comprising said peptide ligands and multimeric binding complexes and the use of said peptide ligands, multimeric binding complexes and pharmaceutical compositions in preventing, suppressing or treating a disease or disorder mediated by TREM2.

BACKGROUND OF THE INVENTION

Cyclic peptides are able to bind with high affinity and specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat. Rev. Drug. Discov. 7(7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å$^2$; Wu et al. (2007), Science 330, 1066-71), a cyclic peptide with the Arg-Gly-Asp motif binding to integrin αVb3 (355 Å$^2$) (Xiong et al. (2002), Science 296(5565), 151-5) or the cyclic peptide inhibitor upain-1 binding to urokinase-type plasminogen activator (603 Å$^2$; Zhao et al. (2007), J. Struct. Biol. 160(1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8 (MMP-8) which lost its selectivity over other MMPs when its ring was opened (Cherney et al. (1998), J. Med. Chem. 41(11), 1749-51). The favourable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example 1,1',1"-(1,3,5-triazinane-1,3,5-triyl)triprop-2-en-1-one (TATA) (Heinis et al. (2014) Angewandte Chemie, International Edition 53(6) 1602-1606).

Phage display-based combinatorial approaches have been developed to generate and screen large libraries of bicyclic peptides to targets of interest (Heinis et al. (2009), Nat. Chem. Biol. 5(7), 502-7 and WO 2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule scaffold.

SUMMARY OF THE INVENTION

According to a first aspect of the invention, there is provided a peptide ligand specific for TREM2 comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

According to a further aspect of the invention, there is provided a multimeric binding complex which comprises at least two bicyclic peptide ligands, wherein said peptide ligands may be the same or different, each of which comprises a peptide ligand specific for TREM2 comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

According to a yet further aspect of the invention, there is provided a pharmaceutical composition comprising a peptide ligand or multimeric binding complex as defined herein in combination with one or more pharmaceutically acceptable excipients.

According to a further aspect of the invention, there is provided a peptide ligand, multimeric binding complex or pharmaceutical composition as defined herein for use in preventing, suppressing or treating a disease or disorder mediated by TREM2.

DETAILED DESCRIPTION OF THE INVENTION

Figure 1:
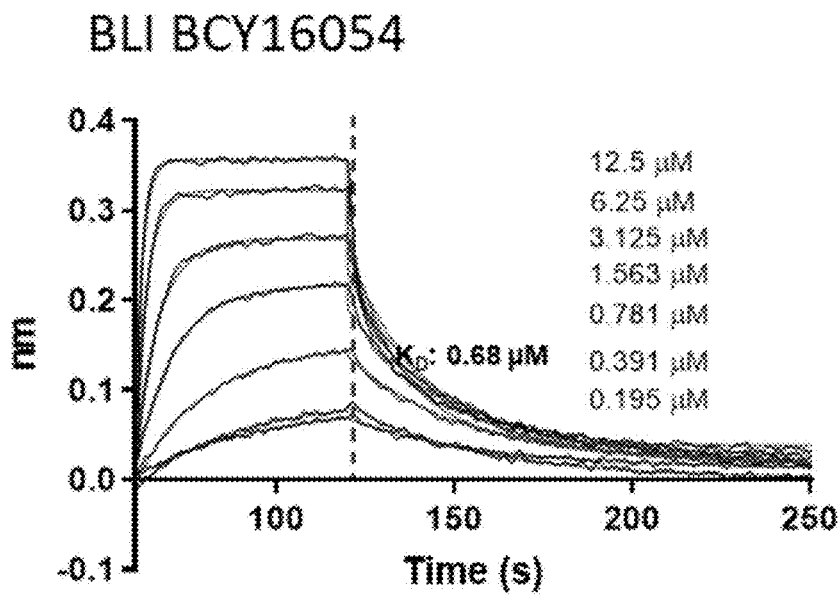
FIG. 1: Bio-Layer Interferometry (BLI) direct binding assay results with selected bicyclic peptides of the invention.
Figure 1:
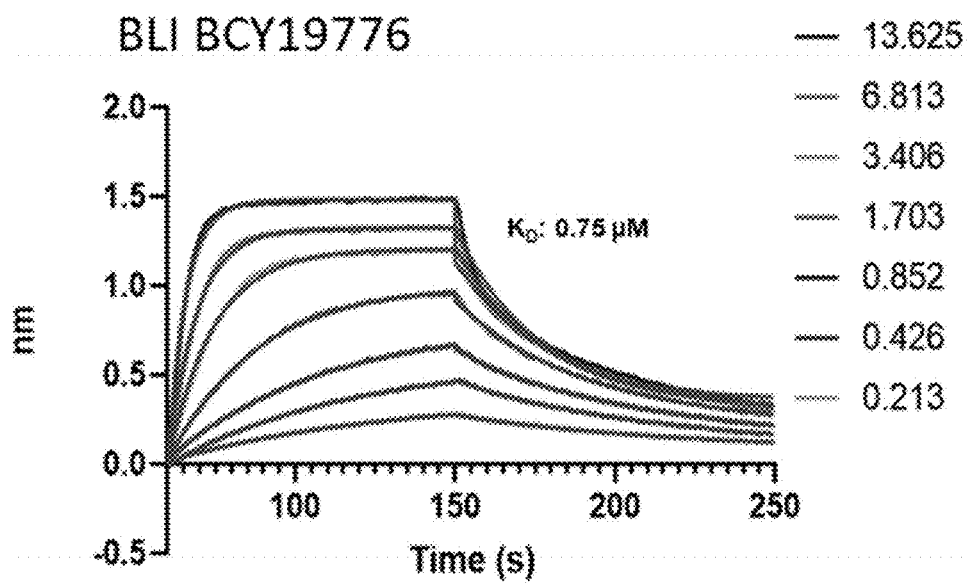

It will be appreciated that the present invention relates to both "monomeric" bicyclic peptides, i.e. those which contain a single (monomeric) bicyclic peptide ligand and "multimeric" bicyclic peptides, i.e. 'those which contain more than one bicyclic peptide (such as 2, 3 or 4) conjugated via one or more linkers.

Monomeric Bicyclic Peptide Ligands

According to a first aspect of the invention, there is provided a peptide ligand specific for TREM2 comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

In one embodiment, said reactive groups comprise cysteine residues.

It will be appreciated that the term "specific for TREM2" refers to the ability of the peptide ligand to bind to TREM2.

In a further embodiment, said loop sequences comprise 3 or 6 amino acids.

In one embodiment, said loop sequences comprise three cysteine residues separated by two loop sequences the first of which consists of 3 amino acids and the second of which consists of 6 amino acids.

In a further embodiment, said loop sequences comprise three cysteine residues separated by two loop sequences the first of which consists of 3 amino acids and the second of which consists of 6 amino acids and comprises an amino acid sequence having the following formula:

(SEQ ID NO: 43)
$C_i\text{-}X_1\text{-}X_2\text{-}X_3\text{-}C_{ii}\text{-}X_4\text{-}X_5\text{-}X_6\text{-}X_7\text{-}X_8\text{-}X_9\text{-}C_{iii}$;

wherein $X_1$ represents an amino acid selected from A, dA, S, T, D, and E, or a non-natural amino acid which is K(pentynoic acid) (K(PYA));

$X_2$ represents an amino acid selected from A, dA, E, Y, S, and N, or a non-natural amino acid which is K(pentynoic acid) (K(PYA));

$X_3$ represents an amino acid selected from A, Y and Q or a non-natural amino acid which is selected from: 2,6-dimethyl-tyrosine (2,6-DiMeTyr), 3,4-dihydroxy-phenylalanine (DOPA), and 3-fluoro-tryptophan (3FTyr);

$X_4$ represents an amino acid selected from I and F or a non-natural amino acid selected from 4-methyl-phenylalanine (4MePhe), homophenylalanine (HPhe), 1-naphthylalanine (1Nal), 2-fluoro-phenylalanine (2FPhe), 3-fluoro-phenylalanine (3FPhe), 4-fluoro-phenylalanine (4FPhe) and 4-pyridylalanine (4Pal);

$X_5$ represents an amino acid selected from R and W or a non-natural amino acid selected from 1-naphthylalanine (1Nal), 2-naphthylalanine (2Nal), 6-chloro-tryptophan (6ClTrp), 5-fluoro-tryptophan (5FTrp), 6-fluoro-tryptophan (6FTrp), 6-methyl-tryptophan (6MeTrp), azatryptophan (AzaTrp), methyl-tryptophan (Trp(Me)), 2-methyl-phenylalanine (2MePhe), 3-methyl-phenylalanine (3MePhe), and trichloromethyl-phenylalanine (4CF3Phe);

$X_6$ represents an amino acid selected from P and A or a non-natural amino acid selected from N-methyl-alanine (NMeAla), aminoisobutyric acid (Aib), pipecolic acid (Pip), azetidine (Aze), Cis-hydroxyproline (Cys-HyP), and 4,4-difluoroproline (44DFP);

$X_7$ represents an amino acid selected from L, F, and Y, or a non-natural amino acid selected from homophenylalanine (HPhe), 2-methyl-phenylalanine (2MePhe), 3-methyl-phenylalanine (3MePhe), 4-methyl-phenylalanine (4MePhe),1-naphthylalanine (1Nal), 2-naphthylalanine (2Nal), 4-fluoro-phenylalanine (4FPhe), t-butyl-alanine (tBuAla), 4,4-biphenylalanine (44BPA), 4-pyridylalanine (4Pal), and K(pentynoic acid) (K(PYA));

$X_8$ represents an amino acid selected from W, Y, F, Q, A, dA, D, and E, or a non-natural amino acid selected from 4-fluoro-phenylalanine (4FPhe), 1-naphthylalanine (1Nal), 2-naphthylalanine (2Nal), 3-t-butyl-tyrosine (3tBuTyr), and K(pentynoic acid) (K(PYA)); and $X_9$ represents an amino acid selected from H, S, P, N, G, Y, Q, W, L, V, A, dA, D, E, and F, or a non-natural amino acid selected from homoarginine (HArg) and K(pentynoic acid) (K(PYA));

wherein $C_i$, $C_{ii}$ and $C_{iii}$ represent first, second and third cysteine residues, respectively, or a pharmaceutically acceptable salt thereof.

In a further embodiment which may be mentioned, said loop sequences comprise three cysteine residues separated by two loop sequences the first of which consists of 3 amino acids and the second of which consists of 6 amino acids and comprises an amino acid sequence having the following formula:

(SEQ ID NO: 43)
$C_i\text{-}X_1\text{-}X_2\text{-}X_3\text{-}C_{ii}\text{-}X_4\text{-}X_5\text{-}X_6\text{-}X_7\text{-}X_8\text{-}X_9\text{-}C_{iii}$;

wherein $X_1$ represents an amino acid selected from A, S and T;

$X_2$ represents an amino acid selected from A, E, Y, S and N;

$X_3$ represents an amino acid selected from A, Y and Q or a non-natural amino acid which is 2,6-dimethyl-tyrosine (2,6-DiMeTyr);

$X_4$ represents an amino acid selected from I and F or a non-natural amino acid selected from 4-methyl-phenylalanine (4MePhe) and homophenylalanine (HPhe);

$X_5$ represents an amino acid selected from R and W or a non-natural amino acid selected from 1-naphthylalanine (1Nal), 2-naphthylalanine (2Nal) and 6-chlorotryptophan (6ClTrp);

$X_6$ represents an amino acid selected from P and A or a non-natural amino acid selected from N-methyl-alanine (NMeAla) and aminoisobutyric acid (Aib);

$X_7$ represents an amino acid selected from L and F or a non-natural amino acid selected from homophenylalanine (HPhe), 4-methyl-phenylalanine (4MePhe) and 1-naphthylalanine (1Nal);

$X_8$ represents an amino acid selected from W, Y, F, Q and A; and $X_9$ represents an amino acid selected from H, S, P, N, G, Y, Q, W, L, V and A;

wherein $C_i$, $C_{ii}$ and $C_{iii}$ represent first, second and third cysteine residues, respectively, or a pharmaceutically acceptable salt thereof.

In a further embodiment, the peptide ligand of SEQ ID NO: 43 comprises an amino acid sequence which is selected from:

(SEQ ID NO: 1; herein referred to as BCY18219)
$C_iSEYC_{ii}FWPFYHC_{iii}$;

(SEQ ID NO: 2)
$C_iSEYC_{ii}FWPFYSC_{iii}$;

(SEQ ID NO: 3)
$C_iSEYC_{ii}FWPFYPC_{iii}$;

(SEQ ID NO: 4)
$C_iSEYC_{ii}FWPFWNC_{iii}$;

(SEQ ID NO: 5)
$C_iSEYC_{ii}FWPLWGC_{iii}$;

(SEQ ID NO: 6)
$C_iSAQC_{ii}IRPFYHC_{iii}$;

(SEQ ID NO: 7)
$C_iSEYC_{ii}FWPLFGC_{iii}$;

(SEQ ID NO: 8)
$C_iSYYC_{ii}FWPFQSC_{iii}$;

(SEQ ID NO: 9)
$C_iSYYC_{ii}FWPFQYC_{iii}$;

(SEQ ID NO: 10)
$C_iTSYC_{ii}FWPFYQC_{iii}$;

(SEQ ID NO: 11)
$C_iTNYC_{ii}FWPFWSC_{iii}$;

(SEQ ID NO: 12)
$C_iSNYC_{ii}FWPFWQC_{iii}$;

(SEQ ID NO: 13)
$C_iSEYC_{ii}FWPFQWC_{iii}$;

(SEQ ID NO: 14)
$C_iSNYC_{ii}FWPFFQC_{iii}$;

(SEQ ID NO: 15)
$C_iSEYC_{ii}FWPFFLC_{iii}$;

(SEQ ID NO: 16)
$C_iSEYC_{ii}FWPFYLC_{iii}$;

(SEQ ID NO: 17)
$C_iSEYC_{ii}FWPFWQC_{iii}$;

(SEQ ID NO: 18)
$C_iTNYC_{ii}FWPFQYC_{iii}$;

(SEQ ID NO: 19)
$C_iTNYC_{ii}FWPFQSC_{iii}$;

(SEQ ID NO: 20)
$C_iTNYC_{ii}FWPFYSC_{iii}$;

(SEQ ID NO: 21)
$C_iTNYC_{ii}FWPFYLC_{iii}$;

(SEQ ID NO: 22)
$C_iTNYC_{ii}FWPFAVC_{iii}$;

(SEQ ID NO: 23)
$C_iSEYC_{ii}FWPFQYC_{iii}$;

(SEQ ID NO: 24)
$C_iAEYC_{ii}FWPFYHC_{iii}$;

(SEQ ID NO: 25)
$C_iSAYC_{ii}FWPFYHC_{iii}$;

(SEQ ID NO: 26)
$C_iSEYC_{ii}FWAFYHC_{iii}$;

(SEQ ID NO: 27)
$C_iSEYC_{ii}FWPFAHC_{iii}$;

(SEQ ID NO: 28)
$C_iSEYC_{ii}FWPFYAC_{iii}$;

(SEQ ID NO: 29)
$C_iSE[2,6-DiMeTyr]C_{ii}FWPFYAC_{iii}$;

(SEQ ID NO: 30)
$C_iSEYC_{ii}[4MePhe]WPFYAC_{iii}$;

(SEQ ID NO: 31)
$C_iSEYC_{ii}[HPhe]WPFYAC_{iii}$;

(SEQ ID NO: 32)
$C_iSEYC_{ii}F[1Nal]PFYAC_{iii}$;

(SEQ ID NO: 33)
$C_iSEYC_{ii}F[2Nal]PFYAC_{iii}$;

(SEQ ID NO: 34)
$C_iSEYC_{ii}FW[NMeAla]FYAC_{iii}$;

(SEQ ID NO: 35)
$C_iSEYC_{ii}FWP[HPhe]YAC_{iii}$;

(SEQ ID NO: 36)
$C_iSEYC_{ii}FWP[4MePhe]YAC_{iii}$;

(SEQ ID NO: 37)
$C_iSEYC_{ii}F[1Nal]PFYHC_{iii}$;

(SEQ ID NO: 38)
$C_iSEYC_{ii}FWP[HPhe]YHC_{iii}$;

(SEQ ID NO: 39)
$C_iSEYC_{ii}F[1Nal]P[HPhe]YHC_{iii}$;

(SEQ ID NO: 40)
$C_iSEYC_{ii}FWP[1Nal]YHC_{iii}$;

(SEQ ID NO: 41)
$C_iSEYC_{ii}FW[Aib]FYHC_{iii}$;

(SEQ ID NO: 42)
$C_iSEYC_{ii}F[6ClTrp]PFYHC_{iii}$;

(SEQ ID NO: 45)
$C_iSEYC_{ii}FWPFFNC_{iii}$;

(SEQ ID NO: 46)
$C_iSEYC_{ii}FWP[1Nal]YAC_{iii}$;

(SEQ ID NO: 47)
$C_iSE[DOPA]C_{ii}FWPFYHC_{iii}$;

(SEQ ID NO: 48)
$C_iSE[3FTyr]C_{ii}FWPFYHC_{iii}$;

(SEQ ID NO: 49)
$C_iSEYC_{ii}[1Nal]WPFYHC_{iii}$;

(SEQ ID NO: 50)
$C_iSEYC_{ii}[4FPhe]WPFYHC_{iii}$;

(SEQ ID NO: 51)
$C_iSEYC_{ii}[2FPhe]WPFYHC_{iii}$;

(SEQ ID NO: 52)
$C_iSEYC_{ii}[3FPhe]WPFYHC_{iii}$;

(SEQ ID NO: 53)
$C_iSEYC_{ii}F[Trp(Me)]PFYHC_{iii}$;

(SEQ ID NO: 54)
$C_iSEYC_{ii}F[6MeTrp]PFYHC_{iii}$;

$C_iSEYC_{ii}F[5FTrp]PFYHC_{iii};$ (SEQ ID NO: 55)

$C_iSEYC_{ii}F[6FTrp]PFYHC_{iii};$ (SEQ ID NO: 56)

$C_iSEYC_{ii}F[3MePhe]PFYHC_{iii};$ (SEQ ID NO: 57)

$C_iSEYC_{ii}F[2Nal]PFYHC_{iii};$ (SEQ ID NO: 58)

$C_iSEYC_{ii}F[AzaTrp]PFYHC_{iii};$ (SEQ ID NO: 59)

$C_iSEYC_{ii}F[CF3Phe]PFYHC_{iii};$ (SEQ ID NO: 60)

$C_iSEYC_{ii}F[2MePhe]PFYHC_{iii};$ (SEQ ID NO: 61)

$C_iSEYC_{ii}FW[Pip]FYHC_{iii};$ (SEQ ID NO: 62)

$C_iSEYC_{ii}FW[44DFP]FYHC_{iii};$ (SEQ ID NO: 63)

$C_iSEYC_{ii}FW[Aze]FYHC_{iii};$ (SEQ ID NO: 64)

$C_iSEYC_{ii}FW[Cis-HyP]FYHC_{iii};$ (SEQ ID NO: 65)

$C_iSEYC_{ii}FWP[2MePhe]YHC_{iii};$ (SEQ ID NO: 66)

$C_iSEYC_{ii}FWP[4FPhe]YHC_{iii};$ (SEQ ID NO: 67)

$C_iSEYC_{ii}FWP[tBuAla]YHC_{iii};$ (SEQ ID NO: 68)

$C_iSEYC_{ii}FWPLYHC_{iii};$ (SEQ ID NO: 69)

$C_iSEYC_{ii}FWP[3MePhe]YHC_{iii};$ (SEQ ID NO: 70)

$C_iSEYC_{ii}FWP[44BPA]YHC_{iii};$ (SEQ ID NO: 71)

$C_iSEYC_{ii}FWP[2Nal]YHC_{iii};$ (SEQ ID NO: 72)

$C_iSEYC_{ii}FWPFWHC_{iii};$ (SEQ ID NO: 73)

$C_iSEYC_{ii}FWPF[4FPhe]HC_{iii};$ (SEQ ID NO: 74)

$C_iSEYC_{ii}FWPF[2Nal]HC_{iii};$ (SEQ ID NO: 75)

$C_iSEYC_{ii}FWPF[3tBuTyr]HC_{iii};$ (SEQ ID NO: 76)

$C_iSEYC_{ii}FWPF[1Nal]HC_{iii};$ (SEQ ID NO: 77)

$C_iSEYC_{ii}FWPFYNC_{iii};$ (SEQ ID NO: 78)

$C_i[dA]EYC_{ii}FWPFYHC_{iii};$ (SEQ ID NO: 79)

$C_iS[dA]YC_{ii}FWPFYHC_{iii};$ (SEQ ID NO: 80)

$C_iSEYC_{ii}FWPF[dA]HC_{iii};$ (SEQ ID NO: 81)

$C_iSEYC_{ii}FWPFY[dA]C_{iii};$ (SEQ ID NO: 82)

$C_i[K(PYA)]EYC_{ii}FWPFYHC_{iii};$ (SEQ ID NO: 83)

$C_iS[K(PYA)]YC_{ii}FWPFYHC_{iii};$ (SEQ ID NO: 84)

$C_iSEYC_{ii}FWP[K(PYA)]YHC_{iii};$ (SEQ ID NO: 85)

$C_iSEYC_{ii}FWPF[K(PYA)]HC_{iii};$ (SEQ ID NO: 86)

$C_iSEYC_{ii}FWPFY[K(PYA)]C_{iii};$ (SEQ ID NO: 87)

$C_iSEYC_{ii}FWP[HPhe]QYC_{iii};$ (SEQ ID NO: 88)

$C_iSEYC_{ii}FWP[1Nal]QYC_{iii};$ (SEQ ID NO: 89)

$C_iDEYC_{ii}FWPFYHC_{iii};$ (SEQ ID NO: 90)

$C_iEEYC_{ii}YWPFYHC_{iii};$ (SEQ ID NO: 91)

$C_iSEYC_{ii}YWPFYHC_{iii};$ (SEQ ID NO: 92)

$C_iSEYC_{ii}[4Pal]WPFYHC_{iii};$ (SEQ ID NO: 93)

$C_iSEYC_{ii}FWPYYHC_{iii};$ (SEQ ID NO: 94)

$C_iSEYC_{ii}FWP[4Pal]YHC_{iii};$ (SEQ ID NO: 95)

$C_iSEYC_{ii}FWPFDHC_{iii};$ (SEQ ID NO: 96)

$C_iSEYC_{ii}FWPFEHC_{iii};$ (SEQ ID NO: 97)

$C_iSEYC_{ii}FWPFYQC_{iii};$ (SEQ ID NO: 98)

$C_iSEYC_{ii}FWPFYDC_{iii};$ (SEQ ID NO: 99)

$C_iSEYC_{ii}FWPFYEC_{iii};$ (SEQ ID NO: 100)

$C_iSEYC_{ii}FWPFY[HArg]C_{iii};$ (SEQ ID NO: 101)
and $C_iSEYC_{ii}FWPFYFC_{iii};$ (SEQ ID NO: 102)

wherein $C_i$, $C_{ii}$ and $C_{iii}$ represent first, second and third cysteine residues, respectively, or a pharmaceutically acceptable salt thereof.

In a further embodiment which may be mentioned, the peptide ligand of SEQ ID NO: 43 comprises an amino acid sequence which is selected from:

$C_iSEYC_{ii}FWPFYHC_{iii};$ (SEQ ID NO: 1; herein referred to as BCY18219)

$C_iSEYC_{ii}FWPFYSC_{iii};$ (SEQ ID NO: 2)

$C_iSEYC_{ii}FWPFYPC_{iii}$; (SEQ ID NO: 3)

$C_iSEYC_{ii}FWPFWNC_{iii}$; (SEQ ID NO: 4)

$C_iSEYC_{ii}FWPLWGC_{iii}$; (SEQ ID NO: 5)

$C_iSAQC_{ii}IRPFYHC_{iii}$; (SEQ ID NO: 6)

$C_iSEYC_{ii}FWPLFGC_{iii}$; (SEQ ID NO: 7)

$C_iSYYC_{ii}FWPFQSC_{iii}$; (SEQ ID NO: 8)

$C_iSYYC_{ii}FWPFQYC_{iii}$; (SEQ ID NO: 9)

$C_iTSYC_{ii}FWPFYQC_{iii}$; (SEQ ID NO: 10)

$C_iTNYC_{ii}FWPFWSC_{iii}$; (SEQ ID NO: 11)

$C_iSNYC_{ii}FWPFWQC_{iii}$; (SEQ ID NO: 12)

$C_iSEYC_{ii}FWPFQWC_{iii}$; (SEQ ID NO: 13)

$C_iSNYC_{ii}FWPFQC_{iii}$; (SEQ ID NO: 14)

$C_iSEYC_{ii}FWPFFLC_{iii}$; (SEQ ID NO: 15)

$C_iSEYC_{ii}FWPFYLC_{iii}$; (SEQ ID NO: 16)

$C_iSEYC_{ii}FWPFWQC_{iii}$; (SEQ ID NO: 17)

$C_iTNYC_{ii}FWPFQYC_{iii}$; (SEQ ID NO: 18)

$C_iTNYC_{ii}FWPFQSC_{iii}$; (SEQ ID NO: 19)

$C_iTNYC_{ii}FWPFYSC_{iii}$; (SEQ ID NO: 20)

$C_iTNYC_{ii}FWPFYLC_{iii}$; (SEQ ID NO: 21)

$C_iTNYC_{ii}FWPFAVC_{iii}$; (SEQ ID NO: 22)

$C_iSEYC_{ii}FWPFQYC_{iii}$; (SEQ ID NO: 23)

$C_iAEYC_{ii}FWPFYHC_{iii}$; (SEQ ID NO: 24)

$C_iSAYC_{ii}FWPFYHC_{iii}$; (SEQ ID NO: 25)

$C_iSEYC_{ii}FWAFYHC_{iii}$; (SEQ ID NO: 26)

$C_iSEYC_{ii}FWPFAHC_{iii}$; (SEQ ID NO: 27)

$C_iSEYC_{ii}FWPFYAC_{iii}$; (SEQ ID NO: 28)

$C_iSE[2,6-DiMeTyr]C_{ii}FWPFYAC_{iii}$; (SEQ ID NO: 29)

$C_iSEYC_{ii}[4MePhe]WPFYAC_{iii}$; (SEQ ID NO: 30)

$C_iSEYC_{ii}[HPhe]WPFYAC_{iii}$; (SEQ ID NO: 31)

$C_iSEYC_{ii}F[1Nal]PFYAC_{iii}$; (SEQ ID NO: 32)

$C_iSEYC_{ii}F[2Nal]PFYAC_{iii}$; (SEQ ID NO: 33)

$C_iSEYC_{ii}FW[NMeAla]FYAC_{iii}$; (SEQ ID NO: 34)

$C_iSEYC_{ii}FWP[HPhe]YAC_{iii}$; (SEQ ID NO: 35)

$C_iSEYC_{ii}FWP[4MePhe]YAC_{iii}$; (SEQ ID NO: 36)

$C_iSEYC_{ii}F[1Nal]PFYHC_{iii}$; (SEQ ID NO: 37)

$C_iSEYC_{ii}FWP[HPhe]YHC_{iii}$; (SEQ ID NO: 38)

$C_iSEYC_{ii}F[1Nal]P[HPhe]YHC_{iii}$; (SEQ ID NO: 39)

$C_iSEYC_{ii}FWP[1Nal]YHC_{iii}$; (SEQ ID NO: 40)

$C_iSEYC_{ii}FW[Aib]FYHC_{iii}$; (SEQ ID NO: 41)

$C_iSEYC_{ii}F[6ClTrp]PFYHC_{iii}$; (SEQ ID NO: 42)
and $C_iSEYC_{ii}FWPFFNC_{iii}$; (SEQ ID NO: 45)

wherein $C_i$, $C_{ii}$ and $C_{iii}$ represent first, second and third cysteine residues, respectively, or a pharmaceutically acceptable salt thereof.

In a further embodiment, said loop sequences comprise three cysteine residues separated by two loop sequences the first of which consists of 3 amino acids and the second of which consists of 6 amino acids and comprises an amino acid sequence having the following formula:

(SEQ ID NO: 44)
$C_i$-S-E-Y-$C_{ii}$-F-W-P-$X_7$-$X_8$-$X_9$-$C_{iii}$;

wherein $X_1$, $X_2$ and $X_3$ represent any amino acid residue, $C_i$, $C_{ii}$ and $C_{iii}$ represent first, second and third cysteine residues, respectively, or a pharmaceutically acceptable salt thereof.

In a further embodiment, $X_7$ represents L or F.
In a further embodiment, $X_8$ represents F, W or Y.
In a further embodiment, $X_9$ represents G, N, P, S or H.
In a further embodiment, said loop sequences comprise three cysteine residues separated by two loop sequences the first of which consists of 3 amino acids and the second of which consists of 6 amino acids and comprise an amino acid sequence which is selected from:

(SEQ ID NO: 1; herein referred to as BCY18219);
$C_iSEYC_{ii}FWPFYHC_{iii}$.

(SEQ ID NO: 2)
$C_iSEYC_{ii}FWPFYSC_{iii}$;

-continued

C$_i$SEYC$_{ii}$FWPFYPC$_{iii}$;  (SEQ ID NO: 3)

C$_i$SEYC$_{ii}$FWPFWNC$_{iii}$;  (SEQ ID NO: 4)

C$_i$SEYC$_{ii}$FWPLWGC$_{iii}$;  (SEQ ID NO: 5)

C$_i$SEYC$_{ii}$FWPLFGC$_{iii}$;  (SEQ ID NO: 7)
and

C$_i$SEYC$_{ii}$FWPFFNC$_{iii}$.  (SEQ ID NO: 45)

In a yet further embodiment, the peptide ligand of SEQ ID NO: 43 comprises a molecular scaffold which is TATA and the peptide ligand comprises N- and/or C-terminal additions, and is selected from:

A-(SEQ ID NO: 1)-A-[Sar$_6$]-[KBiot] (herein referred to as BCY15059);
A-(SEQ ID NO: 1)-A-[Sar$_6$]-[KFI] (herein referred to as BCY15263);
A-(SEQ ID NO: 1)-A (herein referred to as BCY16054);
A-(SEQ ID NO: 1)-A-[K(PYA)] (herein referred to as BCY16821);
[K(PYA)]-(SEQ ID NO: 1) (herein referred to as BCY20042);
Ac-(SEQ ID NO: 1) (herein referred to as BCY18217);
Ac-(SEQ ID NO: 1)-[K(PYA)] (herein referred to as BCY20085);
Ac-A-(SEQ ID NO: 1)-A (herein referred to as BCY18218);
A-(SEQ ID NO: 2)-A (herein referred to as BCY17669);
Ac-(SEQ ID NO: 2) (herein referred to as BCY20084);
A-(SEQ ID NO: 3)-A (herein referred to as BCY17670);
Ac-(SEQ ID NO: 3) (herein referred to as BCY20082);
A-(SEQ ID NO: 4)-A (herein referred to as BCY17671);
A-(SEQ ID NO: 5)-A (herein referred to as BCY17673);
A-(SEQ ID NO: 6)-A (herein referred to as BCY17674);
A-(SEQ ID NO: 7)-A (herein referred to as BCY17675);
A-(SEQ ID NO: 8)-A (herein referred to as BCY19766);
A-(SEQ ID NO: 9)-A (herein referred to as BCY19767);
Ac-(SEQ ID NO: 9) (herein referred to as BCY20221);
A-(SEQ ID NO: 10)-A (herein referred to as BCY19768);
A-(SEQ ID NO: 11)-A (herein referred to as BCY19769);
A-(SEQ ID NO: 12)-A (herein referred to as BCY19770);
A-(SEQ ID NO: 13)-A (herein referred to as BCY19771);
A-(SEQ ID NO: 14)-A (herein referred to as BCY19772);
A-(SEQ ID NO: 15)-A (herein referred to as BCY19776);
Ac-(SEQ ID NO: 15) (herein referred to as BCY20222);
A-(SEQ ID NO: 16)-A (herein referred to as BCY19777);
A-(SEQ ID NO: 17)-A (herein referred to as BCY19778);
A-(SEQ ID NO: 18)-A (herein referred to as BCY19779);
A-(SEQ ID NO: 19)-A (herein referred to as BCY19780);
A-(SEQ ID NO: 20)-A (herein referred to as BCY19781);
A-(SEQ ID NO: 21)-A (herein referred to as BCY19782);
A-(SEQ ID NO: 22)-A (herein referred to as BCY19783);
A-(SEQ ID NO: 23)-A (herein referred to as BCY19784);
Ac-(SEQ ID NO: 23) (herein referred to as BCY20220);
A-(SEQ ID NO: 24)-A (herein referred to as BCY18220);
A-(SEQ ID NO: 25)-A (herein referred to as BCY18221);
A-(SEQ ID NO: 26)-A (herein referred to as BCY18225);
A-(SEQ ID NO: 27)-A (herein referred to as BCY18227);
A-(SEQ ID NO: 28)-A (herein referred to as BCY18228);
Ac-(SEQ ID NO: 28) (herein referred to as BCY19293);
Ac-(SEQ ID NO: 29) (herein referred to as BCY19295);
Ac-(SEQ ID NO: 30) (herein referred to as BCY19298);
Ac-(SEQ ID NO: 31) (herein referred to as BCY19300);
Ac-(SEQ ID NO: 32) (herein referred to as BCY19294);
Ac-(SEQ ID NO: 33) (herein referred to as BCY19296);
Ac-(SEQ ID NO: 34) (herein referred to as BCY19303);
Ac-(SEQ ID NO: 35) (herein referred to as BCY19301);
Ac-(SEQ ID NO: 36) (herein referred to as BCY19299);
Ac-(SEQ ID NO: 37) (herein referred to as BCY19669);
Ac-(SEQ ID NO: 38) (herein referred to as BCY19667);
Ac-(SEQ ID NO: 39) (herein referred to as BCY19672);
Ac-(SEQ ID NO: 40) (herein referred to as BCY19668);
Ac-(SEQ ID NO: 41) (herein referred to as BCY19670);
Ac-(SEQ ID NO: 42) (herein referred to as BCY19671);
A-(SEQ ID NO: 45)-A (herein referred to as BCY17672);
Ac-(SEQ ID NO: 46) (herein referred to as BCY20722);
Ac-(SEQ ID NO: 47) (herein referred to as BCY20045);
Ac-(SEQ ID NO: 48) (herein referred to as BCY20044);
Ac-(SEQ ID NO: 49) (herein referred to as BCY20054);
Ac-(SEQ ID NO: 50) (herein referred to as BCY20053);
Ac-(SEQ ID NO: 51) (herein referred to as BCY20051);
Ac-(SEQ ID NO: 52) (herein referred to as BCY20052);
Ac-(SEQ ID NO: 53) (herein referred to as BCY20059);
Ac-(SEQ ID NO: 54) (herein referred to as BCY20060);
Ac-(SEQ ID NO: 55) (herein referred to as BCY20058);
Ac-(SEQ ID NO: 56) (herein referred to as BCY20057);
Ac-(SEQ ID NO: 57) (herein referred to as BCY20064);
Ac-(SEQ ID NO: 58) (herein referred to as BCY20056);
Ac-(SEQ ID NO: 59) (herein referred to as BCY20062);
Ac-(SEQ ID NO: 60) (herein referred to as BCY20065);
Ac-(SEQ ID NO: 61) (herein referred to as BCY20063);
Ac-(SEQ ID NO: 62) (herein referred to as BCY20069);
Ac-(SEQ ID NO: 63) (herein referred to as BCY20066);
Ac-(SEQ ID NO: 64) (herein referred to as BCY20068);
Ac-(SEQ ID NO: 65) (herein referred to as BCY20067);
Ac-(SEQ ID NO: 66) (herein referred to as BCY20071);
Ac-(SEQ ID NO: 67) (herein referred to as BCY20073);
Ac-(SEQ ID NO: 68) (herein referred to as BCY20074);
Ac-(SEQ ID NO: 69) (herein referred to as BCY20070);
Ac-(SEQ ID NO: 70) (herein referred to as BCY20072);
Ac-(SEQ ID NO: 71) (herein referred to as BCY20075);
Ac-(SEQ ID NO: 72) (herein referred to as BCY20076);
Ac-(SEQ ID NO: 73) (herein referred to as BCY20077);
Ac-(SEQ ID NO: 74) (herein referred to as BCY20078);
Ac-(SEQ ID NO: 75) (herein referred to as BCY20079);
Ac-(SEQ ID NO: 76) (herein referred to as BCY20080);
Ac-(SEQ ID NO: 77) (herein referred to as BCY20081);
Ac-(SEQ ID NO: 78) (herein referred to as BCY20083);
Ac-(SEQ ID NO: 79) (herein referred to as BCY20086);
Ac-(SEQ ID NO: 80) (herein referred to as BCY20087);
Ac-(SEQ ID NO: 81) (herein referred to as BCY20093);
Ac-(SEQ ID NO: 82) (herein referred to as BCY20094);
Ac-(SEQ ID NO: 83) (herein referred to as BCY20095);
Ac-(SEQ ID NO: 84) (herein referred to as BCY20096);
Ac-(SEQ ID NO: 85) (herein referred to as BCY20101);
Ac-(SEQ ID NO: 86) (herein referred to as BCY20102);
Ac-(SEQ ID NO: 87) (herein referred to as BCY20103);
Ac-(SEQ ID NO: 88) (herein referred to as BCY20223);
Ac-(SEQ ID NO: 89) (herein referred to as BCY20224);
Ac-(SEQ ID NO: 90) (herein referred to as BCY20563);
Ac-(SEQ ID NO: 91) (herein referred to as BCY20564);
Ac-(SEQ ID NO: 92) (herein referred to as BCY20566);
Ac-(SEQ ID NO: 93) (herein referred to as BCY20567);
Ac-(SEQ ID NO: 94) (herein referred to as BCY20568);
Ac-(SEQ ID NO: 95) (herein referred to as BCY20569);
Ac-(SEQ ID NO: 96) (herein referred to as BCY20570);
Ac-(SEQ ID NO: 97) (herein referred to as BCY20571);
Ac-(SEQ ID NO: 98) (herein referred to as BCY20572);

Ac-(SEQ ID NO: 99) (herein referred to as BCY20573);
Ac-(SEQ ID NO: 100) (herein referred to as BCY20574);
Ac-(SEQ ID NO: 101) (herein referred to as BCY20575); and
Ac-(SEQ ID NO: 102) (herein referred to as BCY20576);
wherein Ac represents acetyl, Sar represents sarcosine, KBiot represents a biotinylated lysine, KFI represents a fluoresceinated lysine and PYA represents pentynoic acid.

In a yet further embodiment which may be mentioned, the peptide ligand of SEQ ID NO: 43 comprises a molecular scaffold which is TATA and the peptide ligand comprises N- and/or C-terminal additions, and is selected from:
A-(SEQ ID NO: 1)-A-[Sar$_6$]-[KBiot] (herein referred to as BCY15059);
A-(SEQ ID NO: 1)-A-[Sar$_6$]-[KFI] (herein referred to as BCY15263);
A-(SEQ ID NO: 1)-A (herein referred to as BCY16054);
A-(SEQ ID NO: 1)-A-[K(PYA)] (herein referred to as BCY16821);
Ac-(SEQ ID NO: 1) (herein referred to as BCY18217);
Ac-A-(SEQ ID NO: 1)-A (herein referred to as BCY18218);
A-(SEQ ID NO: 2)-A (herein referred to as BCY17669);
A-(SEQ ID NO: 3)-A (herein referred to as BCY17670);
A-(SEQ ID NO: 4)-A (herein referred to as BCY17671);
A-(SEQ ID NO: 5)-A (herein referred to as BCY17673);
A-(SEQ ID NO: 6)-A (herein referred to as BCY17674);
A-(SEQ ID NO: 7)-A (herein referred to as BCY17675);
A-(SEQ ID NO: 8)-A (herein referred to as BCY19766);
A-(SEQ ID NO: 9)-A (herein referred to as BCY19767);
A-(SEQ ID NO: 10)-A (herein referred to as BCY19768);
A-(SEQ ID NO: 11)-A (herein referred to as BCY19769);
A-(SEQ ID NO: 12)-A (herein referred to as BCY19770);
A-(SEQ ID NO: 13)-A (herein referred to as BCY19771);
A-(SEQ ID NO: 14)-A (herein referred to as BCY19772);
A-(SEQ ID NO: 15)-A (herein referred to as BCY19776);
A-(SEQ ID NO: 16)-A (herein referred to as BCY19777);
A-(SEQ ID NO: 17)-A (herein referred to as BCY19778);
A-(SEQ ID NO: 18)-A (herein referred to as BCY19779);
A-(SEQ ID NO: 19)-A (herein referred to as BCY19780);
A-(SEQ ID NO: 20)-A (herein referred to as BCY19781);
A-(SEQ ID NO: 21)-A (herein referred to as BCY19782);
A-(SEQ ID NO: 22)-A (herein referred to as BCY19783);
A-(SEQ ID NO: 23)-A (herein referred to as BCY19784);
A-(SEQ ID NO: 24)-A (herein referred to as BCY18220);
A-(SEQ ID NO: 25)-A (herein referred to as BCY18221);
A-(SEQ ID NO: 26)-A (herein referred to as BCY18225);
A-(SEQ ID NO: 27)-A (herein referred to as BCY18227);
A-(SEQ ID NO: 28)-A (herein referred to as BCY18228);
Ac-(SEQ ID NO: 28) (herein referred to as BCY19293);
Ac-(SEQ ID NO: 29) (herein referred to as BCY19295);
Ac-(SEQ ID NO: 30) (herein referred to as BCY19298);
Ac-(SEQ ID NO: 31) (herein referred to as BCY19300);
Ac-(SEQ ID NO: 32) (herein referred to as BCY19294);
Ac-(SEQ ID NO: 33) (herein referred to as BCY19296);
Ac-(SEQ ID NO: 34) (herein referred to as BCY19303);
Ac-(SEQ ID NO: 35) (herein referred to as BCY19301);
Ac-(SEQ ID NO: 36) (herein referred to as BCY19299);
Ac-(SEQ ID NO: 37) (herein referred to as BCY19669);
Ac-(SEQ ID NO: 38) (herein referred to as BCY19667);
Ac-(SEQ ID NO: 39) (herein referred to as BCY19672);
Ac-(SEQ ID NO: 40) (herein referred to as BCY19668);
Ac-(SEQ ID NO: 41) (herein referred to as BCY19670);
Ac-(SEQ ID NO: 42) (herein referred to as BCY19671); and
A-(SEQ ID NO: 45)-A (herein referred to as BCY17672);
wherein Sar represents sarcosine, KBiot represents a biotinylated lysine, KFI represents a fluoresceinated lysine and PYA represents pentynoic acid.

In a yet further embodiment, the peptide ligand comprises N- and/or C-terminal additions and is selected from:
A-(SEQ ID NO: 1)-A (herein referred to as BCY16054).
A-(SEQ ID NO: 2)-A (herein referred to as BCY17669);
A-(SEQ ID NO: 3)-A (herein referred to as BCY17670);
A-(SEQ ID NO: 4)-A (herein referred to as BCY17671);
A-(SEQ ID NO: 5)-A (herein referred to as BCY17673);
A-(SEQ ID NO: 7)-A (herein referred to as BCY17675); and
A-(SEQ ID NO: 45)-A (herein referred to as BCY17672).

For the purpose of this description, the bicyclic peptides are assumed to be cyclised with TATA and yielding a tri-substituted structure. However, as will be clear from the descriptions of the invention presented herein, cyclisation may be performed with any suitable molecular scaffold which forms covalent bonds with the reactive groups of the polypeptide such that at least two polypeptide loops are formed. Cyclisation occurs on $C_i$, $C_{ii}$, and $C_{iii}$.

In a further embodiment, the pharmaceutically acceptable salt is selected from the free acid or the sodium, potassium, calcium or ammonium salt.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, NY; Ausubel et al., Short Protocols in Molecular Biology (1999) 4$^{th}$ ed., John Wiley & Sons, Inc.), which are incorporated herein by reference.

Multimeric Bicyclic Peptide Ligands

According to a further aspect of the invention, there is provided a multimeric binding complex which comprises at least two bicyclic peptide ligands, wherein said peptide ligands may be the same or different, each of which comprises a peptide ligand specific for TREM2 comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

Thus, in this aspect of the invention the multimeric binding complex comprises at least two (i.e. 2, 3 or 4) of any of the monomeric bicyclic peptide ligands as defined herein.

This aspect of the invention describes a series of multimerized bicyclic peptides with various chemical linkers and hinges of various lengths and rigidity using different sites of attachments within said bicyclic peptide which bind and activate TREM2 with a wide range of potency and efficacy.

It will be appreciated by the skilled person that this aspect of the invention presents multiply arranged (multimeric) bicyclic peptides which provide a synergistic benefit by virtue of the resultant properties of said multimeric binding complexes compared to the corresponding monomeric binding complexes which contain a single bicyclic peptide. For example, the multimeric binding complexes of this aspect of the invention typically have greater levels of binding potency or avidity (as measured herein by Kd values) than their monomeric counterparts. Furthermore, the multimeric binding complexes of the invention are designed to be sufficiently small enough to be cleared by the kidneys.

Without being bound by theory it is believed that multimerized bicyclic peptides are able to activate receptors by homo-crosslinking more than one of the same receptor. Thus, in one embodiment, said bicyclic peptide ligands are specific for the same target within TREM2. In a further embodiment, the multimeric binding complex comprises at least two identical bicyclic peptide ligands. By "identical" it is meant bicyclic peptides having the same amino acid sequence, most critically the same amino acid sequence refers to the binding portion of said bicyclic peptide (for example, the sequence may vary in attachment position). In this embodiment, each of the bicyclic peptides within the multimeric binding complex will bind exactly the same epitope upon the same target of TREM2—the resultant target bound complex will therefore create a homodimer (if the multimeric complex comprises two identical bicyclic peptides), homotrimer (if the multimeric complex comprises three identical bicyclic peptides) or homotetramer (if the multimeric complex comprises four identical bicyclic peptides), etc.

In an alternative embodiment, the multimeric binding complex comprises at least two differing bicyclic peptide ligands. By "differing" it is meant bicyclic peptides having a different amino acid sequence. In this embodiment, the differing bicyclic peptide ligands within the multimeric binding complex will bind to different epitopes on TREM2—the resultant target bound complex will therefore create a biparatopic (if the multimeric complex comprises two differing bicyclic peptides), triparatopic (if the multimeric complex comprises three differing bicyclic peptides) or tetraparatopic (if the multimeric complex comprises four differing bicyclic peptides), etc.

Without being bound by theory it is believed that multimerized bicyclic peptides are able to activate receptors by hetero-crosslinking differing targets, such as differing target receptors on TREM2. Thus, in one embodiment, said bicyclic peptide ligands are specific for different targets on TREM2. It will be appreciated that in this embodiment, the multimeric binding complex comprises at least two differing bicyclic peptide ligands (i.e. bicyclic peptide ligands having differing amino acid sequences). In this embodiment, each of the bicyclic peptides within the multimeric binding complex will bind a differing epitope upon TREM2—the resultant target bound complex will therefore create a bispecific multimeric binding complex (if the multimeric complex comprises two differing bicyclic peptides), trispecific multimeric binding complex (if the multimeric complex comprises three differing bicyclic peptides), tetraspecific multimeric binding complex (if the multimeric complex comprises four differing bicyclic peptides), etc.

It will be appreciated that the multimeric binding complexes of the invention may be designed to be capable of binding to a range of different targets on TREM2, such as receptors.

The bicyclic peptides within the multimeric binding complexes of the invention may be assembled via a number of differing options. For example, there may be a central hinge or branching moiety with spacer or arm elements radiating from said hinge or branch point each of which will contain a bicyclic peptide. Alternatively, it could be envisaged that a circular support member may hold a number of inwardly or outwardly projecting bicyclic peptides.

In one embodiment, each bicyclic peptide ligand is connected to a central hinge moiety by a spacer group.

It will be appreciated that the spacer group may be linear and connect a single bicyclic peptide with the central hinge moiety. Thus, in one embodiment, the multimeric binding complex comprises a compound of formula (I):

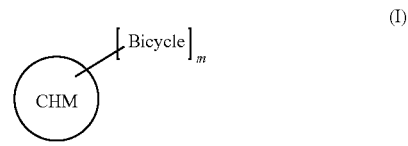

wherein CHM represents a central hinge moiety;
Bicycle represents a bicyclic peptide ligand as defined herein; and
m represents an integer selected from 2 to 10.

In one embodiment, m represents an integer selected from 3 to 10. In a further embodiment, m represents an integer selected from 2, 3 or 4.

In a further embodiment, m represents 2.

When m represents 2, it will be appreciated that the central hinge moiety will require 2 points of attachment. Thus, in one embodiment, m represents 2 and CHM is a motif of formula (A):

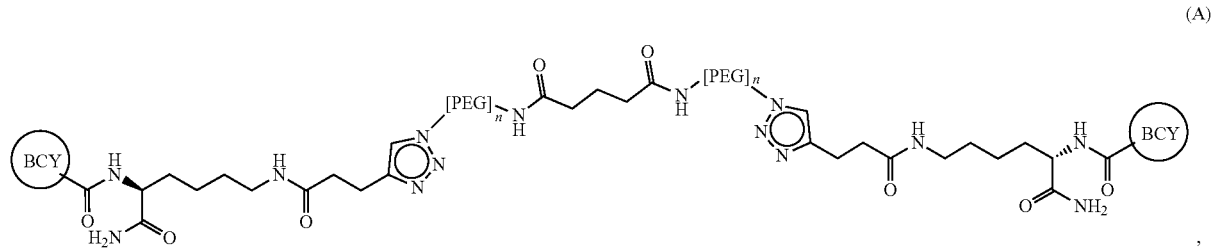

wherein BCY represents a bicyclic peptide ligand as defined herein and n represents a suitable integer for the value of PEG units, such as 1 to 50.

In an alternative embodiment, m represents 3.

When m represents 3, it will be appreciated that the central hinge moiety will require 3 points of attachment. Thus, in one embodiment, m represents 3 and CHM is a motif of formula (B):

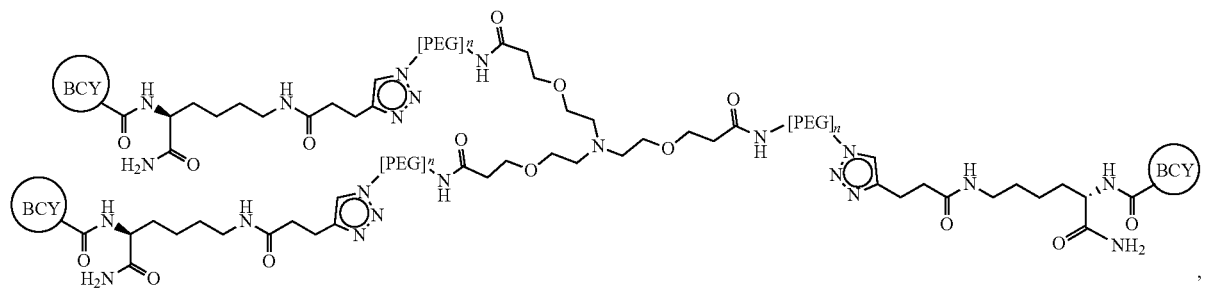

(B)

wherein BCY represents a bicyclic peptide ligand as defined herein and n represents a suitable integer for the value of PEG units, such as 1 to 50.

In an alternative embodiment, m represents 4.

When m represents 4, it will be appreciated that the central hinge moiety will require 4 points of attachment. Thus, in one embodiment, m represents 4 and CHM is a motif of formula (C):

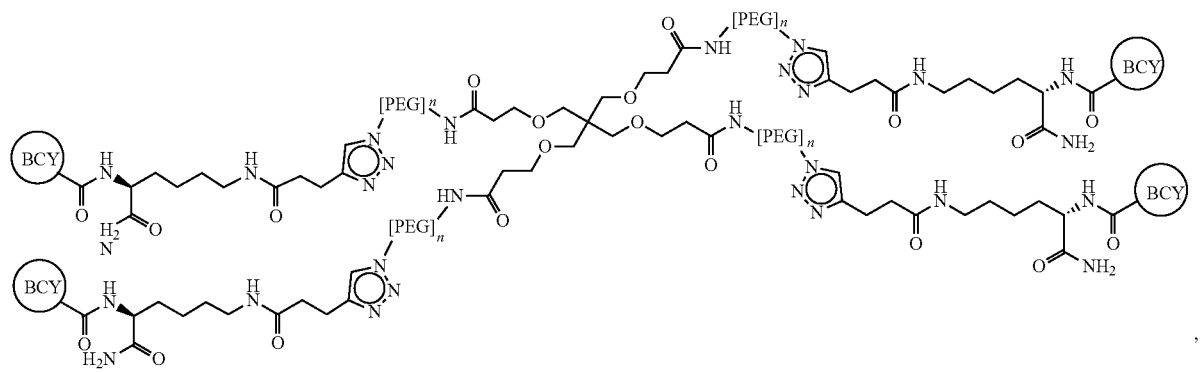

(C)

wherein BCY represents a bicyclic peptide ligand as defined herein and n represents a suitable integer for the value of PEG units, such as 1 to 50.

Dimers

In one embodiment, the multimeric binding complex comprises two identical bicyclic peptides and comprises a dimeric binding complex described in the following Table 1:

TABLE 1

Exemplified Dimeric Binding Complexes of the Invention

| Multimer Compound Number | Corresponding Monomer | Number of Monomers | Central Hinge Moiety | Attachment Point |
|---|---|---|---|---|
| BCY18119 | BCY16821 | 2 | A (PEG$_{10}$) | C-terminus |
| BCY18117 | BCY16821 | 2 | A (PEG$_{23}$) | C-terminus |

BCY18117 and BCY18119 may be represented structurally as:

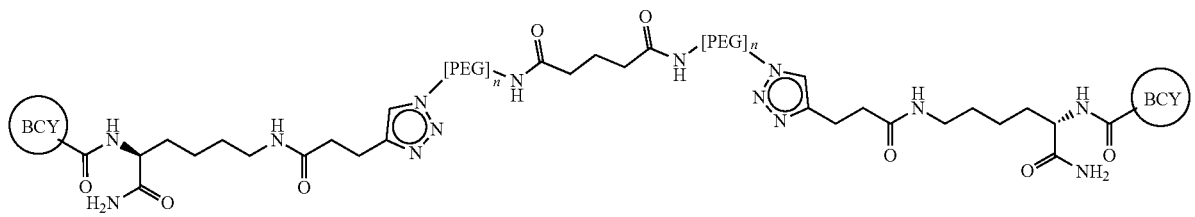

BCY18117 and BCY18119 wherein BCY represents BCY16821 and [PEG]$_n$ represents either PEG$_{10}$ (BCY18119) or PEG$_{23}$ (BCY18117).

Trimers

In an alternative embodiment, the multimeric binding complex comprises three identical bicyclic peptides and comprises a trimeric binding complex described in the following Table 2:

TABLE 2

Exemplified Trimeric Binding Complexes of the Invention

| Multimer Compound Number | Corresponding Monomer | Number of Monomers | Central Hinge Moiety | Attachment Point |
|---|---|---|---|---|
| BCY18122 | BCY16821 | 3 | B (PEG$_{10}$) | C-terminus |
| BCY18118 | BCY16821 | 3 | B (PEG$_{23}$) | C-terminus |

BCY18118 and BCY18122 may be represented structurally as:

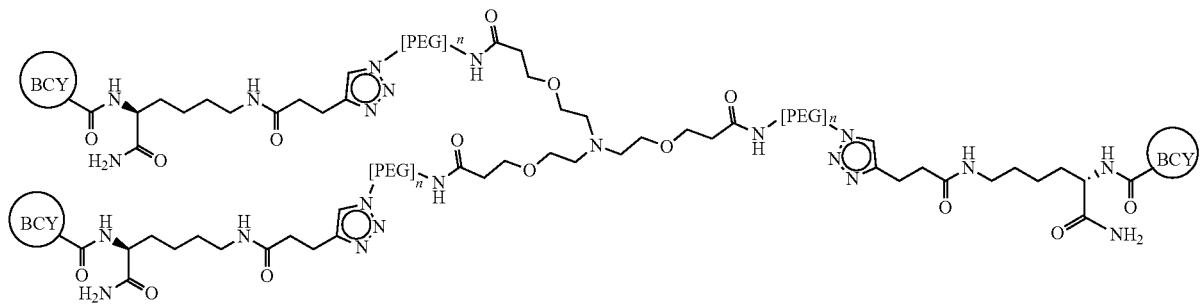

BCY18118 and BCY18122 wherein BCY represents BCY16821 and [PEG]$_n$ represents PEG$_{10}$ (BCY18122) or PEG$_{23}$ (BCY18118).

Tetramers

In one embodiment, the multimeric binding complex comprises four identical bicyclic peptides and comprises a tetrameric binding complex described in the following Table 3:

TABLE 3

Exemplified Tetrameric Binding Complexes of the Invention

| Multimer Compound Number | Corresponding Monomer | Number of Monomers | Central Hinge Moiety | Attachment Point |
|---|---|---|---|---|
| BCY18121 | BCY16821 | 4 | C (PEG$_{10}$) | C-terminus |
| BCY18120 | BCY16821 | 4 | C (PEG$_{23}$) | C-terminus |

BCY18120 and 18121 may be represented structurally as:

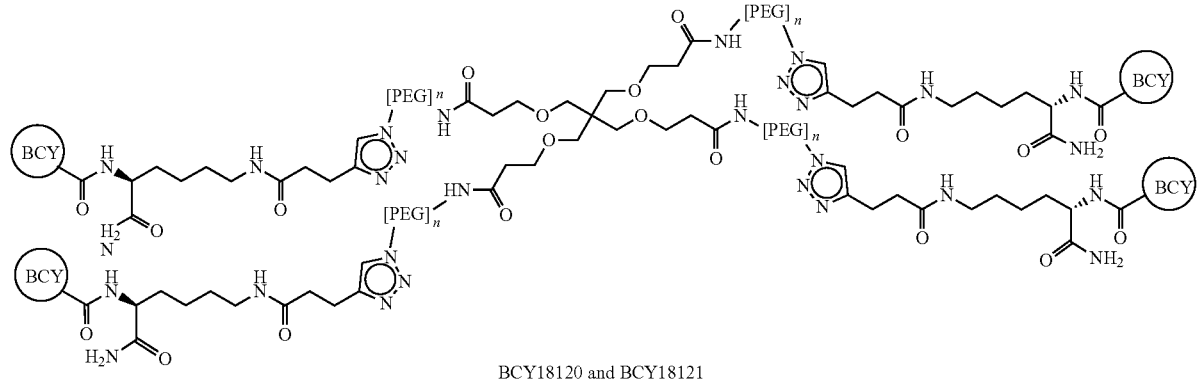

BCY18120 and BCY18121 wherein BCY represents BCY16821 and [PEG]$_n$ represents PEG$_{10}$ (BCY18121) or PEG$_{23}$ (BCY18120).

Numbering

When referring to amino acid residue positions within the peptides of the invention, cysteine residues ($C_i$, $C_{ii}$ and $C_{iii}$) are omitted from the numbering as they are invariant, therefore, the numbering of amino acid residues within the peptides of the invention is referred to as below:

(SEQ ID NO: 1)
-$C_i$-$S_1$-$E_2$-$Y_3$-$C_{ii}$-$F_4$-$W_5$-$P_6$-$F_7$-$Y_8$-$H_9$-$C_{iii}$-.

Molecular Format

N- or C-terminal extensions to the bicycle core sequence are added to the left or right side of the sequence, separated by a hyphen. For example, an N-terminal biotin-G-Sar$_5$ tail would be denoted as:

(SEQ ID NO: X)
[Biot]-G-[Sar$_5$]-A-.

Inversed Peptide Sequences

In light of the disclosure in Nair et al. (2003) J. Immunol. 170(3), 1362-1373, it is envisaged that the peptide sequences disclosed herein would also find utility in their retro-inverso form.

For example, the sequence is reversed (i.e. N-terminus become C-terminus and vice versa) and their stereochemistry is likewise also reversed (i.e. D-amino acids become L-amino acids and vice versa).

Peptide Ligand Definition

A peptide ligand, as referred to herein, refers to a peptide, peptidic or peptidomimetic covalently bound to a molecular scaffold. Typically, such peptides, peptidics or peptidomimetics comprise a peptide having natural or non-natural amino acids, two or more reactive groups (i.e. cysteine residues) which are capable of forming covalent bonds to the scaffold, and a sequence subtended between said reactive groups which is referred to as the loop sequence, since it forms a loop when the peptide, peptidic or peptidomimetic is bound to the scaffold. In the present case, the peptides, peptidics or peptidomimetics comprise at least three cysteine residues (referred to herein as $C_i$, $C_{ii}$ and $C_{iii}$), and form at least two loops on the scaffold.

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide ligands should in most circumstances demonstrate stability to plasma proteases, epithelial ("membrane-anchored") proteases, gastric and intestinal proteases, lung surface proteases, intracellular proteases and the like. Protease stability should be maintained between different species such that a bicyclic peptide lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes; and An optimal plasma half-life in the circulation. Depending upon the clinical indication and treatment regimen, it may be required to develop a bicyclic peptide with short or prolonged in vivo exposure times for the management of either chronic or acute disease states. The optimal exposure time will be governed by the requirement for sustained exposure (for maximal therapeutic efficiency) versus the requirement for short exposure times to minimise toxicological effects arising from sustained exposure to the agent.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g. —COOH may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the peptides of the invention contain an amine function, these may form quaternary ammonium salts, for example by reaction with an alkylating agent according to methods well known to the skilled person. Such quaternary ammonium compounds are within the scope of the peptides of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with one or more replacement amino acids, such as an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group; modification of amino acids such as cysteine, lysine, glutamate/aspartate and tyrosine with suitable amine, thiol, carboxylic acid and phenol-reactive reagents so as to functionalise said amino acids; and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal residue is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal residue is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acids. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al. (2005) PNAS, 102(2), 413-418).

In one embodiment, the modified derivative comprises removal of any amino acid residues and substitution with alanines, such as D-alanines. This embodiment provides the advantage of identifying key binding residues and removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al., *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al., Curr. Pharmaceutical Design, (2010), 16, 3185-203, and Nestor et al., Curr. Medicinal Chem (2009), 16, 4399-418).

Isotopic Variations

The present invention includes all pharmaceutically acceptable (radio)isotope-labelled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, sulphur, such as $^{35}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled peptide ligands of the invention, for example, those incorporating a radioactive isotope, are useful in drug and/or substrate tissue distribution studies, and to clinically assess the presence and/or absence of the target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labelled compounds of peptide ligands of the invention can generally be prepared by conventional techniques known to those skilled in the art or by processes analogous to those described in the accompanying Examples using an appropriate isotopically-labelled reagent in place of the non-labelled reagent previously employed.

Molecular Scaffold

In one embodiment, the molecular scaffold comprises a non-aromatic molecular scaffold. References herein to "non-aromatic molecular scaffold" refers to any molecular scaffold as defined herein which does not contain an aromatic (i.e. unsaturated) carbocyclic or heterocyclic ring system.

Suitable examples of non-aromatic molecular scaffolds are described in Heinis et al. (2014) Angewandte Chemie, International Edition 53(6) 1602-1606.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold is 1,1',1''-(1,3,5-triazinane-1,3,5-triyl)triprop-2-en-1-one (also known as triacryloylhexahydro-s-triazine (TATA):

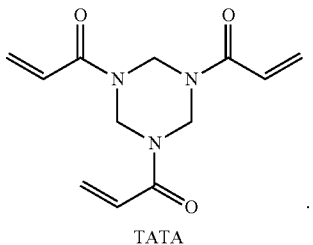

TATA

Thus, following cyclisation with the bicyclic peptides of the invention on the $C_i$, $C_{ii}$, and $C_{iii}$ cysteine residues, the molecular scaffold forms a tri-substituted 1,1',1''-(1,3,5-triazinane-1,3,5-triyl)tripropan-1-one derivative of TATA having the following structure:

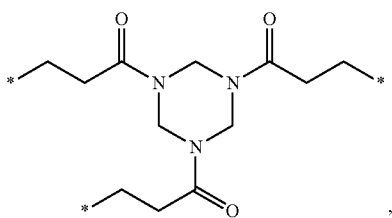 [SMILES: *CCC(=O)N1CN(C(=O)CC*)CN(C(=O)CC*)C1]

wherein * denotes the point of attachment of the three cysteine residues.

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al. (supra).

Thus, the invention also relates to the manufacture of polypeptides or conjugates selected as set out herein, wherein the manufacture comprises optional further steps as explained below.

In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al. Proc Natl Acad Sci USA. 1994 Dec. 20; 91(26):12544-8 or in Hikari et al. Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TATA) could be added during the chemical synthesis of the first peptide so as to react with the three cysteine groups; a further cysteine or thiol could then be appended to the N- or C-terminus of the first peptide, so that this cysteine or thiol only reacted with a free cysteine or thiol of the second peptide, forming a disulphide-linked bicyclic peptide-peptide conjugate.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand or multimeric binding complex as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringers dextrose, dextrose and sodium chloride and lactated Ringers. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringers dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cyclosporine, methotrexate, adriamycin or cisplatinum and immunotoxins. Further examples of other agents which may be administered separately or in conjunction with the peptide ligands of the invention include cytokines, lymphokines, other hematopoietic factors, thrombolytic and anti-thrombotic factors. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered intravenously. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as TREM2 binding agents. According to a further aspect of the invention, there is provided a peptide ligand or pharmaceutical composition as defined herein for use in preventing, suppressing or treating a disease or disorder mediated by TREM2.

TREM2 is also known as "triggering receptor expressed on myeloid cells 2" and is a protein that in humans is encoded by the TREM2 gene. TREM2 is a transmembrane receptor of the immunoglobulin superfamily. The ligands of TREM2 encompass a wide array of anionic molecules, free and bound to the plasma membrane, including bacterial products, DNA, lipoproteins, and phospholipids. TREM2 consists of an extracellular domain that includes a single V-type immunoglobulin domain, a short ectodomain, a single transmembrane helix, and a short cytosolic tail that lacks any signal transduction or trafficking motifs. Instead, studies on mouse macrophages showed that TREM2 associates with the adaptor proteins DNAX activation protein 12 (DAP12) and DAP10 via oppositely charged residues in their transmembrane domains. Upon TREM2-ligand interaction, these co-receptors are phosphorylated and recruit intracellular signal transduction machinery. DAP12, also known as TYRO protein tyrosine kinase-binding protein (TYROBP), mediates activation of spleen tyrosine kinase Syk, whereas DAP10 promotes signal propagation by recruiting phosphatidylinositol 3-kinase (PI3K). TREM2 can bind DAP12 or DAP10 and possibly form TREM2-DAP12-DAP10 heterodimers (Peng et al., 2010). Downstream signaling is critically dependent on these arrangements; for example, in mouse macrophages, DAP12 is required for $Ca^{2+}$ mobilization, whereas DAP10 is critical for activation of serine/threonine protein kinase (AKT1) and extracellular signal-regulated kinase (ERK).

TREM2 has recently been linked with a number of disorders, notably Alzheimer's disease, obesity-related metabolic syndrome, and cancer (Deczkowska et al (2020) Cell 181, 1207-1217). This reference provides a clear link between TREM2 binding agents and the following disorders: inflammatory disorders, neurological disorders such as Alzheimer's disease, cancer, molecular disorders such as obesity, fatty liver and atherosclerosis. Thus, in one embodiment, the disease or disorder mediated by TREM2 is selected from: inflammatory disorders, neurological disorders such as Alzheimer's disease, cancer, molecular disorders such as obesity, fatty liver and atherosclerosis. In a further embodiment, the cancer is selected from: bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

In an alternative embodiment, the disease or disorder mediated by TREM2 is selected from: dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, In a further embodiment, the disease or disorder mediated by TREM2 is selected from: dementia, frontotemporal dementia, Alzheimer's disease, Nasu-Hakola disease, and multiple sclerosis.

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

Materials and Methods
Preparation of Bicyclic Peptide Ligands (General Method)

Bicycle peptides were synthesized on Rink amide resin using standard Fmoc (9-fluorenylmethyloxycarbonyl) solid-phase peptide synthesis, either by manual coupling (for large scale) or using a Biotage Syroll automated peptide synthesizer (for small scale). Following TFA-based cleavage from the resin, peptides were precipitated with diethyl ether and dissolved in 50:50 acetonitrile/water. The crude peptides (at ~1 mM concentration) were then cyclized with 1.3 equiv. of the scaffold, using ammonium bicarbonate (100 mM) as a base. Completion of cyclization was determined by matrix-assisted laser desorption ionization time-of-flight (MALDI-TOF) or LC-MS. Once complete, the cyclization reaction was quenched using N-acetyl cysteine (10 equiv. with respect to the peptide), and the solutions were lyophilized. The residue was dissolved in an appropriate solvent and purified by RP-HPLC. Peptide fractions of sufficient purity and the correct molecular weight (verified by either MALDI-TOF and HPLC or LC-MS) were pooled and lyophilized. Concentrations were determined by UV absorption using the extinction coefficient at 280 nm, which was based on Trp/Tyr content.

All amino acids, unless noted otherwise, were used in the L-configurations.

Biological Data
1. Bio-Layer Interferometry (BLI) Direct Binding Assay

Bio-layer interferometry was performed on an Octet RED384® system (Sartorius) at 25° C. in a buffer containing 50 mM HEPES (pH 7.5), 150 mM NaCl and 0.1% Tween. TREM2 extracellular domain (ECD) (residues 19-131, C-terminally biotinylated, deglycosylated or glycosylated) was loaded onto Superstreptavidin biosensors (SSA, 18-5070, Sartorius) at 0.0125 mg/ml for 300 s. Bicycle peptides (10 mM in DMSO) were dispensed into 384-Well Tilted-Bottom Plates (18-5076, Sartorius) using an Echo liquid handler giving a final DMSO concentration of 0.125% in all wells including control wells. Association of defined concentrations of bicyclic peptide (0-12.5 μM, 1:2 dilutions for 7 points) was recorded over 120 s followed by dissociation in buffer over 120 s. Reference wells containing no bicycle peptides and reference sensors loaded with an unrelated protein (His-tagged MLLT3a) were subjected to the same assay protocol and double reference subtraction was used for processing to account for non-specific binding. Traces were analysed using Octet Software (Version 11.0). Association and dissociation curves were globally fit and the response at equilibrium (Req) plotted against concentration to obtain steady-state KD values.

Selected peptides of the invention were tested in the above mentioned assay and the results are shown in Tables 4A and 4B:

TABLE 4A

Human and Cyno BLI Binding Assay Results for Selected Peptide Ligands of the Invention

| BCY No. | Human BLI (Kd; nM) (deglycosylated) | Cyno BLI (Kd; nM) |
|---|---|---|
| 17675 | 3300 | nt |
| 17673 | 1600 | nt |
| 17672 | 2000 | nt |
| 17671 | 900 | nt |
| 17670 | 1700 | nt |
| 17669 | 1200 | nt |
| 16054 | 700 | 3300 |
| 19766 | 1000 | nt |
| 19767 | 550 | nt |
| 19768 | 900 | nt |
| 19769 | 920 | nt |
| 19770 | 1800 | nt |
| 19771 | 5700 | nt |
| 19772 | 960 | nt |
| 19776 | 750 | nt |
| 19777 | ~1200 | nt |
| 19778 | 3600 | nt |
| 19779 | 920 | nt |
| 19780 | 2400 | nt |
| 19781 | 1400 | nt |
| 19782 | 1400 | nt |
| 19783 | 2700 | nt |
| 19784 | 450 | nt |
| 18217 | 900 | nt |
| 18218 | 2000 | nt |
| 18219 | 700 | nt |
| 18220 | 2000 | nt |
| 18221 | 1800 | nt |
| 18225 | 14000 | nt |
| 18227 | 3100 | nt |
| 18228 | 2600 | nt |
| 19293 | 970 | nt |
| 19295 | 51000 | nt |
| 19298 | 3400 | nt |
| 19300 | 42000 | nt |
| 19294 | 1500 | nt |
| 19296 | 2700 | nt |
| 19303 | 2300 | nt |
| 19301 | 460 | nt |
| 19299 | 18000 | nt |
| 19669 | 2000 | nt |
| 19667 | 430 | nt |
| 19672 | 2800 | nt |
| 19668 | 240 | nt |
| 19670 | 30000 | nt |
| 19671 | 1000 | nt | nt = not tested

TABLE 4B

Human and Cyno BLI Binding Assay Results for Selected Peptide Ligands of the Invention

| BCY No. | Human BLI (Kd; nM) (deglycosylated) | Human BLI (Kd; nM) glycosylated | Cyno BLI (Kd; nM) |
|---|---|---|---|
| 20722 | 390 | 770 | 3600 |
| 20045 | 405 | 260 | nt |
| 20044 | 3040 | nt | nt |
| 20054 | 2540 | 1830 | nt |
| 20053 | 2010 | 1710 | nt |
| 20051 | 2035 | nt | nt |
| 20052 | 4880 | 1250 | nt |
| 20059 | 1810 | 1500 | nt |
| 20060 | 1390 | 1110 | nt |
| 20058 | 1430 | nt | nt |
| 20057 | 2555 | nt | nt |
| 20064 | 5240 | nt | nt |
| 20056 | 4690 | nt | nt |
| 20062 | 3440 | nt | nt |
| 20065 | 7280 | nt | nt |
| 20063 | 1300 | 1580 | nt |
| 20069 | 1460 | nt | nt |
| 20066 | 1860 | 980 | nt |
| 20068 | 2535 | nt | nt |
| 20067 | 23600 | nt | nt |
| 20071 | 910 | 780 | nt |
| 20073 | 2320 | 2130 | nt |
| 20074 | 1630 | 920 | nt |
| 20070 | 1665 | nt | nt |
| 20072 | 1670 | nt | nt |
| 20075 | 2400 | 1510 | nt |
| 20076 | nt | 1290 | nt |
| 20077 | nt | 750 | nt |
| 20078 | nt | 1410 | nt |
| 20079 | nt | 880 | nt |
| 20080 | 375 | nt | nt |
| 20081 | 1060 | nt | nt |
| 20082 | 1930 | nt | nt |
| 20083 | 1835 | nt | nt |
| 20084 | 1650 | nt | nt |
| 20086 | 17950 | nt | nt |
| 20087 | 18020 | nt | nt |
| 20093 | 4685 | nt | nt |
| 20094 | 2530 | nt | nt |
| 20042 | 1190 | 1350 | nt |
| 20095 | 5270 | nt | nt |
| 20096 | 2500 | 3790 | nt |
| 20101 | 18600 | nt | nt |
| 20102 | 1465 | nt | nt |
| 20103 | 1150 | nt | nt |
| 20085 | 1620 | nt | nt |
| 20220 | 1305 | nt | nt |
| 20221 | 690 | nt | nt |
| 20222 | 1570 | nt | nt |
| 20223 | 470 | nt | nt |
| 20224 | 455 | nt | nt |
| 20563 | 3170 | nt | nt |
| 20564 | 3120 | nt | nt |
| 20566 | 2140 | nt | nt |
| 20567 | 1020 | nt | nt |
| 20568 | 2280 | nt | nt |
| 20569 | 3800 | nt | nt |
| 20570 | 1870 | nt | nt |
| 20571 | 2210 | nt | nt |
| 20572 | 1060 | nt | nt |
| 20573 | 1960 | nt | nt |
| 20574 | 1740 | nt | nt |
| 20575 | 375 | nt | nt |
| 20576 | 1350 | nt | nt | nt = not tested

Further data is presented herein in FIGS. 1A to 1D where it can be seen that BCY16054 shows binding to the human TREM2 extracellular domain in the BLI (biolayer interferometry) assay with a $K_D$ of ~700 nM.

2. pSYK Homogenous Time Resolved Fluorescence (HTRF) Assay

Quantitative assessment of total and phospho (Tyr 525/526) SYK was performed on iPSC macrophages using CisBio total and phospho-SYK HTRF kits (catalogue numbers 64SYKTPGG and 64SYKY525-PEG respectively). Human iPSC macrophage precursors derived from embryoid bodies were plated in 96 well plates (Perkin Elmer Cell Carrier ultra, black walled plates, #6055800) at a density of 40 k cells per well in 100 μl macrophage media (XVIVO15 (Lonza, #BE04-418F), 1% Penicillin-Streptomycin (Gibco, #15140-122), 1% GlutaMAX™ Supplement (Gibco, #35050-038), 0.1% M-CSF (Invitrogen, #PHC9501)). Cells were grown for 7 days to induce full differentiation to iPSC macrophages. Both parental (TREM2 expressing) and isogenic TREM2 KO iPSC macrophages were plated to test for specificity of peptide binding. Following differentiation, cells were stimulated for 5 mins with either the control TREM2 activating antibody (R&D systems, #AF1828), a human IgG control (R&D systems, #AB-108-C), or a 10 point CRC of bicyclic peptide (serial 2 fold dilutions from a starting concentration of 100 μM). Following stimulation the media was removed, and cells were lysed in 50 μl lysis buffer (supplied with the kit) per well. Cells were incubated in LB3 for 30 mins with shaking at room temperature. Following lysis, 16 μl of sample was removed and added to a white 384 well plate (ProxiPlate-384 Plus (Perkin Elmer, #6008280)) and 4 μl of pre-mixed antibody solution was added to each well of the plate. The plate was incubated overnight at room temperature, and the following day, absorbance was measured at 665 nm and 620 nm using a Pherastar FSX. The same cell lysate was used to assess total and phosphorylated SYK, to enable the generation of a ratio of phosphorylated SYK in each sample.

Selected peptides of the invention were tested in the above mentioned assay and the results are shown in Table 5:

TABLE 5 pSYK Assay Results for Selected Peptide Ligands of the Invention

| BCY No | pSYK (μM) |
|---|---|
| 16054 | 10.69 |
| 19766 | 35.2 |
| 19767 | 8.6 |
| 19768 | 7.8 |
| 19769 | 0.2 |
| 19770 | 4.5 |
| 19771 | 9.9 |
| 19772 | 13.9 |
| 19776 | 4.4 |
| 19778 | 4.6 |
| 19779 | 2.5 |
| 19780 | 12.6 |
| 19781 | 34.1 |
| 19782 | 3.8 |
| 19783 | 4.2 |
| 19784 | 1.8 |
| 19293 | 7.2 |
| 19295 | NB |
| 19298 | <3.4 |
| 19300 | >10 |
| 19294 | <3.4 |

TABLE 5-continued pSYK Assay Results for Selected Peptide Ligands of the Invention

| BCY No | pSYK (µM) |
|---|---|
| 19296 | <3.4 |
| 19303 | <3.4 |
| 19301 | <3.4 |
| 19299 | >10 |
| 19669 | 16.6 |
| 19667 | 7.4 |
| 19672 | 8.5 |
| 19668 | 12.7 |
| 19670 | NB |
| 19671 | 154.4 |

NB = no binding

Figure 2:
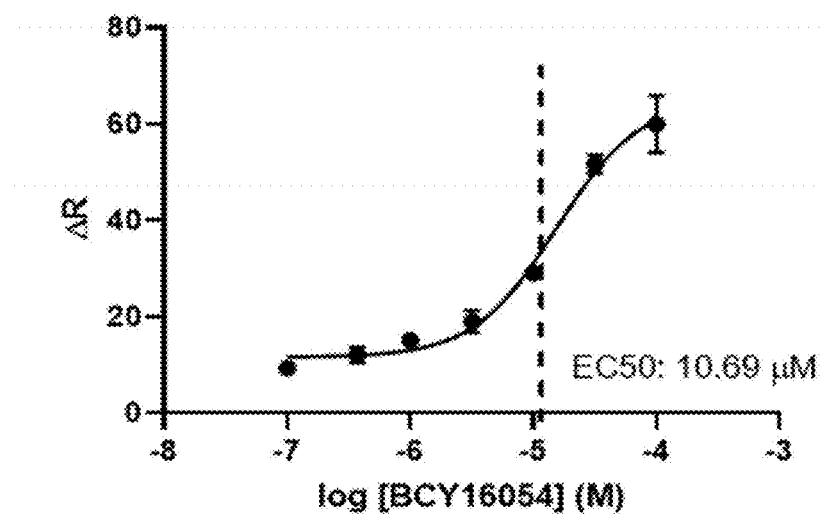
FIG. 2: pSYK Homogenous time resolved fluorescence (HTRF) assay results with selected bicyclic peptides of the invention.
Figure 2:
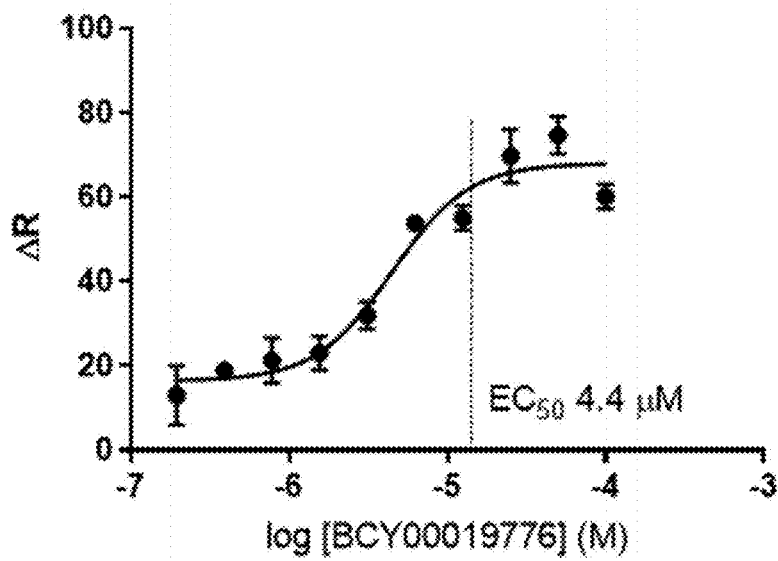

Further data is presented herein in FIGS. 2A to 2D where it can be seen that BCY16054 demonstrated a concentration dependent increase in phosphoSYK with an $EC_{50}$ of 10.69 µM indicating that BCY16054 has agonist activity at the TREM2 receptor. Results shown with other bicyclic peptides showed a range of activities that were broadly in line with their affinities from the BLI assay.

The invention claimed is:

1. A peptide ligand specific for triggering receptor expressed on myeloid cells 2 (TERM2) comprising a polypeptide comprising at least three reactive groups, separated by at least two loop sequences, and a molecular scaffold which forms covalent bonds with the reactive groups of the polypeptide such that at least two polypeptide loops are formed on the molecular scaffold, wherein the peptide ligand comprises an amino acid sequence having the following formula:

$C_i$-$X_1$-$X_2$-$X_3$-$C_{ii}$-$X_4$-$X_5$-$X_6$-$X_7$-$X_8$-$X_9$-$C_{iii}$    (SEQ ID NO: 43);

wherein:
- $X_1$ represents an amino acid selected from A, dA, S, T, D, and E, or a non-natural amino acid which is K(pentynoic acid) (K(PYA));
- $X_2$ represents an amino acid selected from A, dA, E, Y, S, and N, or a non-natural amino acid which is K(pentynoic acid) (K(PYA));
- $X_3$ represents an amino acid selected from A, Y and Q or a non-natural amino acid which is selected from: 2,6-dimethyl-tyrosine (2,6-DiMeTyr), 3,4-dihydroxy-phenylalanine (DOPA), and 3-fluoro-tryptophan (3FTyr);
- $X_4$ represents an amino acid selected from I and F or a non-natural amino acid selected from 4-methyl-phenylalanine (4MePhe), homophenylalanine (HPhe), 1-naphthylalanine (1Nal), 2-fluoro-phenylalanine (2FPhe), 3-fluoro-phenylalanine (3FPhe), 4-fluoro-phenylalanine (4FPhe) and 4-pyridylalanine (4Pal);
- $X_5$ represents an amino acid selected from R and W or a non-natural amino acid selected from 1-naphthylalanine (1Nal), 2-naphthylalanine (2Nal), 6-chloro-tryptophan (6ClTrp), 5-fluoro-tryptophan (5FTrp), 6-fluoro-tryptophan (6FTrp), 6-methyl-tryptophan (6MeTrp), azatryptophan (AzaTrp), methyl-tryptophan (Trp(Me)), 2-methyl-phenylalanine (2MePhe), 3-methyl-phenylalanine (3MePhe), and trichloromethyl-phenylalanine (4CF3Phe);
- $X_6$ represents an amino acid selected from P and A or a non-natural amino acid selected from N-methyl-alanine (NMeAla), aminoisobutyric acid (Aib), pipecolic acid (Pip), azetidine (Aze), Cis-hydroxyproline (Cys-HyP), and 4,4-difluoroproline (44DFP);
- $X_7$ represents an amino acid selected from L, F, and Y, or a non-natural amino acid selected from homophenylalanine (HPhe), 2-methyl-phenylalanine (2MePhe), 3-methyl-phenylalanine (3MePhe), 4-methyl-phenylalanine (4MePhe), 1-naphthylalanine (1Nal), 2-naphthylalanine (2Nal), 4-fluoro-phenylalanine (4FPhe), t-butyl-alanine (tBuAla), 4,4-biphenylalanine (44BPA), 4-pyridylalanine (4Pal), and K(pentynoic acid) (K(PYA));
- $X_8$ represents an amino acid selected from W, Y, F, Q, A, dA, D, and E, or a non-natural amino acid selected from 4-fluoro-phenylalanine (4FPhe), 1-naphthylalanine (1Nal), 2-naphthylalanine (2Nal), 3-t-butyl-tyrosine (3tBuTyr), and K(pentynoic acid) (K(PYA)); and
- $X_9$ represents an amino acid selected from H, S, P, N, G, Y, Q, W, L, V, A, dA, D, E, and F, or a non-natural amino acid selected from homoarginine (HArg) and K(pentynoic acid) (K(PYA));

wherein $C_i$, $C_{ii}$ and $C_{iii}$ represent first, second and third cysteine residues, respectively, or a pharmaceutically acceptable salt thereof.

2. The peptide ligand according to claim 1, wherein the peptide ligand of SEQ ID NO: 43 comprises an amino acid sequence which is selected from:

(SEQ ID NO: 1; herein referred to as BCY18219)
$C_i$SEYC$_{ii}$FWPFYHC$_{iii}$;

(SEQ ID NO: 2)
$C_i$SEYC$_{ii}$FWPFYSC$_{iii}$;

(SEQ ID NO: 3)
$C_i$SEYC$_{ii}$FWPFYPC$_{iii}$;

(SEQ ID NO: 4)
$C_i$SEYC$_{ii}$FWPFWNC$_{iii}$;

(SEQ ID NO: 5)
$C_i$SEYC$_{ii}$FWPLWGC$_{iii}$;

(SEQ ID NO: 6)
$C_i$SAQC$_{ii}$IRPFYHC$_{iii}$;

(SEQ ID NO: 7)
$C_i$SEYC$_{ii}$FWPLFGC$_{iii}$;

(SEQ ID NO: 8)
$C_i$SYYC$_{ii}$FWPFQSC$_{iii}$;

(SEQ ID NO: 9)
$C_i$SYYC$_{ii}$FWPFQYC$_{iii}$;

(SEQ ID NO: 10)
$C_i$TSYC$_{ii}$FWPFYQC$_{iii}$;

(SEQ ID NO: 11)
$C_i$TNYC$_{ii}$FWPFWSC$_{iii}$;

(SEQ ID NO: 12)
$C_i$SNYC$_{ii}$FWPFWQC$_{iii}$;

(SEQ ID NO: 13)
$C_i$SEYC$_{ii}$FWPFQWC$_{iii}$;

(SEQ ID NO: 14)
$C_i$SNYC$_{ii}$FWPFFQC$_{iii}$;

(SEQ ID NO: 15)
$C_i$SEYC$_{ii}$FWPFFLC$_{iii}$;

(SEQ ID NO: 16)
$C_i$SEYC$_{ii}$FWPFYLC$_{iii}$;

(SEQ ID NO: 17)
$C_i$SEYC$_{ii}$FWPFWQC$_{iii}$;

(SEQ ID NO: 18)
$C_i$TNYC$_{ii}$FWPFQYC$_{iii}$;

(SEQ ID NO: 19)
$C_i$TNYC$_{ii}$FWPFQSC$_{iii}$;

(SEQ ID NO: 20)
$C_i$TNYC$_{ii}$FWPFYSC$_{iii}$;

(SEQ ID NO: 21)
$C_i$TNYC$_{ii}$FWPFYLC$_{iii}$;

(SEQ ID NO: 22)
$C_i$TNYC$_{ii}$FWPFAVC$_{iii}$;

(SEQ ID NO: 23)
$C_i$SEYC$_{ii}$FWPFQYC$_{iii}$;

(SEQ ID NO: 24)
$C_i$AEYC$_{ii}$FWPFYHC$_{iii}$;

(SEQ ID NO: 25)
$C_i$SAYC$_{ii}$FWPFYHC$_{iii}$;

(SEQ ID NO: 26)
$C_i$SEYC$_{ii}$FWAFYHC$_{iii}$;

(SEQ ID NO: 27)
$C_i$SEYC$_{ii}$FWPFAHC$_{iii}$;

(SEQ ID NO: 28)
$C_i$SEYC$_{ii}$FWPFYAC$_{iii}$;

(SEQ ID NO: 29)
$C_i$SE[2,6-DiMeTyr]C$_{ii}$FWPFYAC$_{iii}$;

(SEQ ID NO: 30)
$C_i$SEYC$_{ii}$[4MePhe]WPFYAC$_{iii}$;

(SEQ ID NO: 31)
$C_i$SEYC$_{ii}$[HPhe]WPFYAC$_{iii}$;

(SEQ ID NO: 32)
$C_i$SEYC$_{ii}$F[1Nal]PFYAC$_{iii}$;

(SEQ ID NO: 33)
$C_i$SEYC$_{ii}$F[2Nal]PFYAC$_{iii}$;

(SEQ ID NO: 34)
$C_i$SEYC$_{ii}$FW[NMeAla]FYAC$_{iii}$;

(SEQ ID NO: 35)
$C_i$SEYC$_{ii}$FWP[HPhe]YAC$_{iii}$;

(SEQ ID NO: 36)
$C_i$SEYC$_{ii}$FWP[4MePhe]YAC$_{iii}$;

(SEQ ID NO: 37)
$C_i$SEYC$_{ii}$F[1Nal]PFYHC$_{iii}$;

(SEQ ID NO: 38)
$C_i$SEYC$_{ii}$FWP[HPhe]YHC$_{iii}$;

(SEQ ID NO: 39)
$C_i$SEYC$_{ii}$F[1Nal]P[HPhe]YHC$_{iii}$;

(SEQ ID NO: 40)
$C_i$SEYC$_{ii}$FWP[1Nal]YHC$_{iii}$;

(SEQ ID NO: 41)
$C_i$SEYC$_{ii}$FW[Aib]FYHC$_{iii}$;

(SEQ ID NO: 42)
$C_i$SEYC$_{ii}$F[6ClTrp]PFYHC$_{iii}$;

(SEQ ID NO: 45)
$C_i$SEYC$_{ii}$FWPFFNC$_{iii}$;

(SEQ ID NO: 46)
$C_i$SEYC$_{ii}$FWP[1Nal]YAC$_{iii}$;

(SEQ ID NO: 47)
$C_i$SE[DOPA]C$_{ii}$FWPFYHC$_{iii}$;

(SEQ ID NO: 48)
$C_i$SE[3FTyr]C$_{ii}$FWPFYHC$_{iii}$;

(SEQ ID NO: 49)
$C_i$SEYC$_{ii}$[1Nal]WPFYHC$_{iii}$;

(SEQ ID NO: 50)
$C_i$SEYC$_{ii}$[4FPhe]WPFYHC$_{iii}$;

(SEQ ID NO: 51)
$C_i$SEYC$_{ii}$[2FPhe]WPFYHC$_{iii}$;

(SEQ ID NO: 52)
$C_i$SEYC$_{ii}$[3FPhe]WPFYHC$_{iii}$;

(SEQ ID NO: 53)
$C_i$SEYC$_{ii}$F[Trp(Me)]PFYHC$_{iii}$;

(SEQ ID NO: 54)
$C_i$SEYC$_{ii}$F[6MeTrp]PFYHC$_{iii}$;

(SEQ ID NO: 55)
$C_i$SEYC$_{ii}$F[5FTrp]PFYHC$_{iii}$;

(SEQ ID NO: 56)
$C_i$SEYC$_{ii}$F[6FTrp]PFYHC$_{iii}$;

(SEQ ID NO: 57)
$C_i$SEYC$_{ii}$F[3MePhe]PFYHC$_{iii}$;

(SEQ ID NO: 58)
$C_i$SEYC$_{ii}$F[2Nal]PFYHC$_{iii}$;

(SEQ ID NO: 59)
$C_i$SEYC$_{ii}$F[AzaTrp]PFYHC$_{iii}$;

(SEQ ID NO: 60)
$C_i$SEYC$_{ii}$F[CF3Phe]PFYHC$_{iii}$;

(SEQ ID NO: 61)
$C_i$SEYC$_{ii}$F[2MePhe]PFYHC$_{iii}$;

(SEQ ID NO: 62)
$C_i$SEYC$_{ii}$FW[Pip]FYHC$_{iii}$;

(SEQ ID NO: 63)
$C_i$SEYC$_{ii}$FW[44DFP]FYHC$_{iii}$;

(SEQ ID NO: 64)
$C_i$SEYC$_{ii}$FW[Aze]FYHC$_{iii}$;

(SEQ ID NO: 65)
$C_i$SEYC$_{ii}$FW[Cis-HyP]FYHC$_{iii}$;

(SEQ ID NO: 66)
$C_i$SEYC$_{ii}$FWP[2MePhe]YHC$_{iii}$;

(SEQ ID NO: 67)
$C_i$SEYC$_{ii}$FWP[4FPhe]YHC$_{iii}$;

(SEQ ID NO: 68)
$C_i$SEYC$_{ii}$FWP[tBuAla]YHC$_{iii}$;

(SEQ ID NO: 69)
$C_i$SEYC$_{ii}$FWPLYHC$_{iii}$;

(SEQ ID NO: 70)
$C_i$SEYC$_{ii}$FWP[3MePhe]YHC$_{iii}$;

(SEQ ID NO: 71)
$C_i$SEYC$_{ii}$FWP[44BPA]YHC$_{iii}$;

(SEQ ID NO: 72)
$C_i$SEYC$_{ii}$FWP[2Nal]YHC$_{iii}$;

(SEQ ID NO: 73)
$C_i$SEYC$_{ii}$FWPFWHC$_{iii}$;

$C_iSEYC_{ii}FWPF[4FPhe]HC_{iii}$; (SEQ ID NO: 74)

$C_iSEYC_{ii}FWPF[2Nal]HC_{iii}$; (SEQ ID NO: 75)

$C_iSEYC_{ii}FWPF[3tBuTyr]HC_{iii}$; (SEQ ID NO: 76)

$C_iSEYC_{ii}FWPF[1Nal]HC_{iii}$; (SEQ ID NO: 77)

$C_iSEYC_{ii}FWPFYNC_{iii}$; (SEQ ID NO: 78)

$C_i[dA]EYC_{ii}FWPFYHC_{iii}$; (SEQ ID NO: 79)

$C_iS[dA]YC_{ii}FWPFYHC_{iii}$; (SEQ ID NO: 80)

$C_iSEYC_{ii}FWPF[dA]HC_{iii}$; (SEQ ID NO: 81)

$C_iSEYC_{ii}FWPFY[dA]C_{iii}$; (SEQ ID NO: 82)

$C_i[K(PYA)]EYC_{ii}FWPFYHC_{iii}$; (SEQ ID NO: 83)

$C_iS[K(PYA)]YC_{ii}FWPFYHC_{iii}$; (SEQ ID NO: 84)

$C_iSEYC_{ii}FWP[K(PYA)]YHC_{iii}$; (SEQ ID NO: 85)

$C_iSEYC_{ii}FWPF[K(PYA)]HC_{iii}$; (SEQ ID NO: 86)

$C_iSEYC_{ii}FWPFY[K(PYA)]C_{iii}$; (SEQ ID NO: 87)

$C_iSEYC_{ii}FWP[HPhe]QYC_{iii}$; (SEQ ID NO: 88)

$C_iSEYC_{ii}FWP[1Nal]QYC_{iii}$; (SEQ ID NO: 89)

$C_iDEYC_{ii}FWPFYHC_{iii}$; (SEQ ID NO: 90)

$C_iEEYC_{ii}YWPFYHC_{iii}$; (SEQ ID NO: 91)

$C_iSEYC_{ii}YWPFYHC_{iii}$; (SEQ ID NO: 92)

$C_iSEYC_{ii}[4Pal]WPFYHC_{iii}$; (SEQ ID NO: 93)

$C_iSEYC_{ii}FWPYYHC_{iii}$; (SEQ ID NO: 94)

$C_iSEYC_{ii}FWP[4Pal]YHC_{iii}$; (SEQ ID NO: 95)

$C_iSEYC_{ii}FWPFDHC_{iii}$; (SEQ ID NO: 96)

$C_iSEYC_{ii}FWPFEHC_{iii}$; (SEQ ID NO: 97)

$C_iSEYC_{ii}FWPFYQC_{iii}$; (SEQ ID NO: 98)

$C_iSEYC_{ii}FWPFYDC_{iii}$; (SEQ ID NO: 99)

$C_iSEYC_{ii}FWPFYEC_{iii}$; (SEQ ID NO: 100)

$C_iSEYC_{ii}FWPFY[HArg]C_{iii}$; (SEQ ID NO: 101)

and $C_iSEYC_{ii}FWPFYFC_{iii}$; (SEQ ID NO: 102)

wherein $C_i$, $C_{ii}$ and $C_{iii}$ represent first, second and third cysteine residues, respectively, or a pharmaceutically acceptable salt thereof.

3. The peptide ligand according to claim 1, wherein the pharmaceutically acceptable salt is selected from the free acid or the sodium, potassium, calcium or ammonium salt.

4. A pharmaceutical composition which comprises the peptide ligand according to claim 1, in combination with one or more pharmaceutically acceptable excipients.

5. The peptide ligand according to claim 1, wherein the peptide ligand of SEQ ID NO: 43 comprises a molecular scaffold which is 1,1',1''-(1,3,5-triazinane-1,3,5-triyl)triprop-2-en-1-one (TATA) and the peptide ligand comprises N- and/or C-terminal additions, and is selected from:

A-(SEQ ID NO: 1)-A-[Sar$_6$]-[KBiot] (herein referred to as BCY15059);

A-(SEQ ID NO: 1)-A-[Sar$_6$]-[KF1] (herein referred to as BCY15263);

A-(SEQ ID NO: 1)-A (herein referred to as BCY16054);

A-(SEQ ID NO: 1)-A-[K(PYA)] (herein referred to as BCY16821);

[K(PYA)]-(SEQ ID NO: 1) (herein referred to as BCY20042);

Ac-(SEQ ID NO: 1) (herein referred to as BCY18217);

Ac-(SEQ ID NO: 1)-[K(PYA)] (herein referred to as BCY20085);

Ac-A-(SEQ ID NO: 1)-A (herein referred to as BCY18218);

A-(SEQ ID NO: 2)-A (herein referred to as BCY17669);

Ac-(SEQ ID NO: 2) (herein referred to as BCY20084);

A-(SEQ ID NO: 3)-A (herein referred to as BCY17670);

Ac-(SEQ ID NO: 3) (herein referred to as BCY20082);

A-(SEQ ID NO: 4)-A (herein referred to as BCY17671);

A-(SEQ ID NO: 5)-A (herein referred to as BCY17673);

A-(SEQ ID NO: 6)-A (herein referred to as BCY17674);

A-(SEQ ID NO: 7)-A (herein referred to as BCY17675);

A-(SEQ ID NO: 8)-A (herein referred to as BCY19766);

A-(SEQ ID NO: 9)-A (herein referred to as BCY19767);

Ac-(SEQ ID NO: 9) (herein referred to as BCY20221);

A-(SEQ ID NO: 10)-A (herein referred to as BCY19768);

A-(SEQ ID NO: 11)-A (herein referred to as BCY19769);

A-(SEQ ID NO: 12)-A (herein referred to as BCY19770);

A-(SEQ ID NO: 13)-A (herein referred to as BCY19771);

A-(SEQ ID NO: 14)-A (herein referred to as BCY19772);

A-(SEQ ID NO: 15)-A (herein referred to as BCY19776);

Ac-(SEQ ID NO: 15) (herein referred to as BCY20222);

A-(SEQ ID NO: 16)-A (herein referred to as BCY19777);

A-(SEQ ID NO: 17)-A (herein referred to as BCY19778);

A-(SEQ ID NO: 18)-A (herein referred to as BCY19779);

A-(SEQ ID NO: 19)-A (herein referred to as BCY19780);

A-(SEQ ID NO: 20)-A (herein referred to as BCY19781);

A-(SEQ ID NO: 21)-A (herein referred to as BCY19782);

A-(SEQ ID NO: 22)-A (herein referred to as BCY19783);

A-(SEQ ID NO: 23)-A (herein referred to as BCY19784);

Ac-(SEQ ID NO: 23) (herein referred to as BCY20220);

A-(SEQ ID NO: 24)-A (herein referred to as BCY18220);

A-(SEQ ID NO: 25)-A (herein referred to as BCY18221);

A-(SEQ ID NO: 26)-A (herein referred to as BCY18225);

A-(SEQ ID NO: 27)-A (herein referred to as BCY18227);

A-(SEQ ID NO: 28)-A (herein referred to as BCY18228);

Ac-(SEQ ID NO: 28) (herein referred to as BCY19293);

Ac-(SEQ ID NO: 29) (herein referred to as BCY19295);

Ac-(SEQ ID NO: 30) (herein referred to as BCY19298);

Ac-(SEQ ID NO: 31) (herein referred to as BCY19300);

Ac-(SEQ ID NO: 32) (herein referred to as BCY19294);

Ac-(SEQ ID NO: 33) (herein referred to as BCY19296);

Ac-(SEQ ID NO: 34) (herein referred to as BCY19303);

Ac-(SEQ ID NO: 35) (herein referred to as BCY19301);

Ac-(SEQ ID NO: 36) (herein referred to as BCY19299);

Ac-(SEQ ID NO: 37) (herein referred to as BCY19669);

Ac-(SEQ ID NO: 38) (herein referred to as BCY19667);

Ac-(SEQ ID NO: 39) (herein referred to as BCY19672);

Ac-(SEQ ID NO: 40) (herein referred to as BCY19668);

Ac-(SEQ ID NO: 41) (herein referred to as BCY19670);

Ac-(SEQ ID NO: 42) (herein referred to as BCY19671);

A-(SEQ ID NO: 45)-A (herein referred to as BCY17672);

Ac-(SEQ ID NO: 46) (herein referred to as BCY20722);

Ac-(SEQ ID NO: 47) (herein referred to as BCY20045);

Ac-(SEQ ID NO: 48) (herein referred to as BCY20044);

Ac-(SEQ ID NO: 49) (herein referred to as BCY20054);

Ac-(SEQ ID NO: 50) (herein referred to as BCY20053);

Ac-(SEQ ID NO: 51) (herein referred to as BCY20051);

Ac-(SEQ ID NO: 52) (herein referred to as BCY20052);

Ac-(SEQ ID NO: 53) (herein referred to as BCY20059);

Ac-(SEQ ID NO: 54) (herein referred to as BCY20060);

Ac-(SEQ ID NO: 55) (herein referred to as BCY20058);

Ac-(SEQ ID NO: 56) (herein referred to as BCY20057);

Ac-(SEQ ID NO: 57) (herein referred to as BCY20064);

Ac-(SEQ ID NO: 58) (herein referred to as BCY20056);

Ac-(SEQ ID NO: 59) (herein referred to as BCY20062);

Ac-(SEQ ID NO: 60) (herein referred to as BCY20065);

Ac-(SEQ ID NO: 61) (herein referred to as BCY20063);

-continued

Ac-(SEQ ID NO: 62) (herein referred to as BCY20069);

Ac-(SEQ ID NO: 63) (herein referred to as BCY20066);

Ac-(SEQ ID NO: 64) (herein referred to as BCY20068);

Ac-(SEQ ID NO: 65) (herein referred to as BCY20067);

Ac-(SEQ ID NO: 66) (herein referred to as BCY20071);

Ac-(SEQ ID NO: 67) (herein referred to as BCY20073);

Ac-(SEQ ID NO: 68) (herein referred to as BCY20074);

Ac-(SEQ ID NO: 69) (herein referred to as BCY20070);

Ac-(SEQ ID NO: 70) (herein referred to as BCY20072);

Ac-(SEQ ID NO: 71) (herein referred to as BCY20075);

Ac-(SEQ ID NO: 72) (herein referred to as BCY20076);

Ac-(SEQ ID NO: 73) (herein referred to as BCY20077);

Ac-(SEQ ID NO: 74) (herein referred to as BCY20078);

Ac-(SEQ ID NO: 75) (herein referred to as BCY20079);

Ac-(SEQ ID NO: 76) (herein referred to as BCY20080);

Ac-(SEQ ID NO: 77) (herein referred to as BCY20081);

Ac-(SEQ ID NO: 78) (herein referred to as BCY20083);

Ac-(SEQ ID NO: 79) (herein referred to as BCY20086);

Ac-(SEQ ID NO: 80) (herein referred to as BCY20087);

Ac-(SEQ ID NO: 81) (herein referred to as BCY20093);

Ac-(SEQ ID NO: 82) (herein referred to as BCY20094);

Ac-(SEQ ID NO: 83) (herein referred to as BCY20095);

Ac-(SEQ ID NO: 84) (herein referred to as BCY20096);

Ac-(SEQ ID NO: 85) (herein referred to as BCY20101);

Ac-(SEQ ID NO: 86) (herein referred to as BCY20102);

Ac-(SEQ ID NO: 87) (herein referred to as BCY20103);

Ac-(SEQ ID NO: 88) (herein referred to as BCY20223);

-continued

Ac-(SEQ ID NO: 89) (herein referred to as BCY20224);

Ac-(SEQ ID NO: 90) (herein referred to as BCY20563);

Ac-(SEQ ID NO: 91) (herein referred to as BCY20564);

Ac-(SEQ ID NO: 92) (herein referred to as BCY20566);

Ac-(SEQ ID NO: 93) (herein referred to as BCY20567);

Ac-(SEQ ID NO: 94) (herein referred to as BCY20568);

Ac-(SEQ ID NO: 95) (herein referred to as BCY20569);

Ac-(SEQ ID NO: 96) (herein referred to as BCY20570);

Ac-(SEQ ID NO: 97) (herein referred to as BCY20571);

Ac-(SEQ ID NO: 98) (herein referred to as BCY20572);

Ac-(SEQ ID NO: 99) (herein referred to as BCY20573);

Ac-(SEQ ID NO: 100) (herein referred to as BCY20574);

Ac-(SEQ ID NO: 101) (herein referred to as BCY20575);
and

Ac-(SEQ ID NO: 102) (herein referred to as BCY20576);

wherein Ac represents acetyl, Sar represents sarcosine, KBiot represents a biotinylated lysine, KF1 represents a fluoresceinated lysine and PYA represents pentynoic acid.

6. A multimeric binding complex which comprises at least two of the peptide ligands according to claim 1.

7. The multimeric binding complex according to claim 6, which comprises a compound of formula (I):

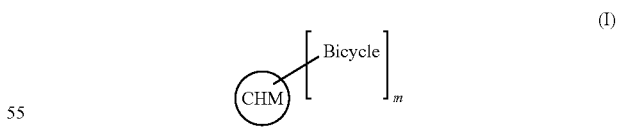

wherein CHM represents a central hinge moiety;

wherein "Bicycle" in formula (I) represents a bicyclic peptide ligand specific for TREM2 comprising a polypeptide comprising at least three reactive groups, separated by at least two loop sequences, and a molecular scaffold which forms covalent bonds with the reactive groups of the polypeptide such that at least two polypeptide loops are formed on the molecular scaffold; and m represents an integer selected from 2 to 10.

8. The multimeric binding complex according to claim 7 wherein m represents 2 and CHM is a motif of formula (A):

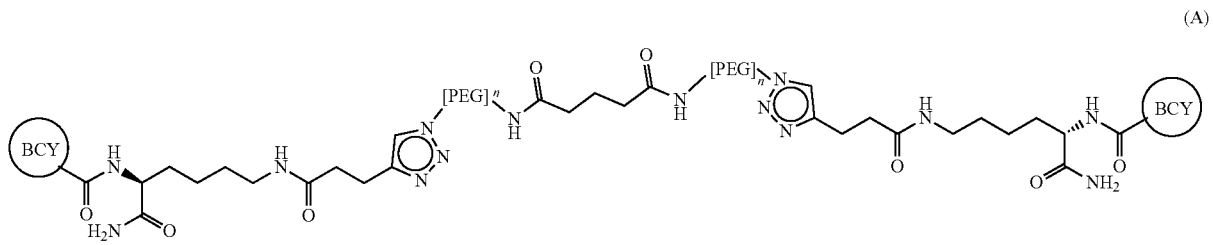

(A)

wherein BCY represents a peptide ligand specific for TREM2 comprising a polypeptide comprising at least three reactive groups, separated by at least two loop sequences, and a molecular scaffold which forms covalent bonds with the reactive groups of the polypeptide such that at least two polypeptide loops are formed on the molecular scaffold and n represents 1 to 50, optionally wherein the multimeric binding complex is BCY18117 and BCY18119:

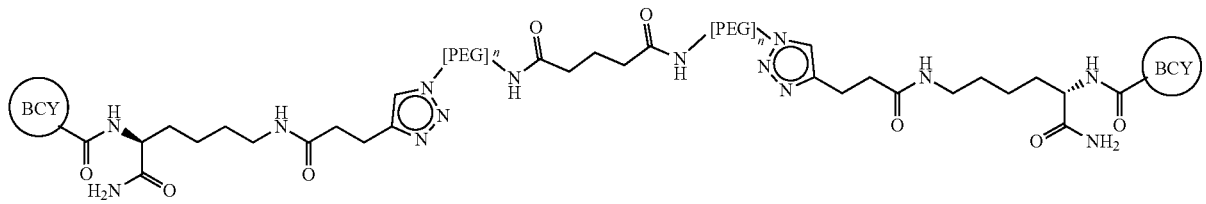

wherein BCY represents
a peptide ligand of SEQ ID NO: 43 comprising a molecular scaffold which is 1,1',1"-(1,3,5-triazinane-1,3,5-triyl)triprop-2-en-1-one (TATA) and the peptide ligand comprises A-(SEQ ID NO: 1)-A-[K(PYA)] and n represents 10 (BCY18119) and 23 (BCY18117).

9. The multimeric binding complex according to claim 7 wherein m represents 3 and CHM is a motif of formula (B):

(B)

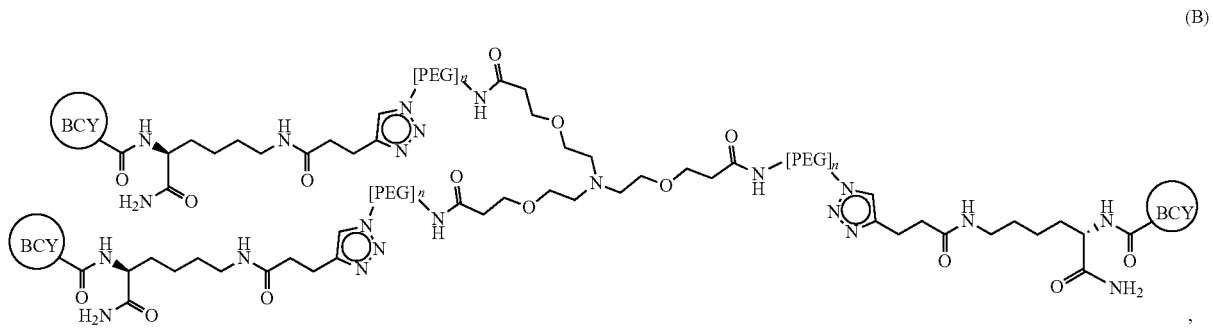

wherein BCY represents a bicyclic peptide ligand specific for TREM2 comprising a polypeptide comprising at least three reactive groups, separated by at least two loop sequences, and a molecular scaffold which forms covalent bonds with the reactive groups of the polypeptide such that at least two polypeptide loops are formed on the molecular scaffold and n represents 1 to 50, optionally wherein the multimeric binding complex is BCY18118 and BCY18122:

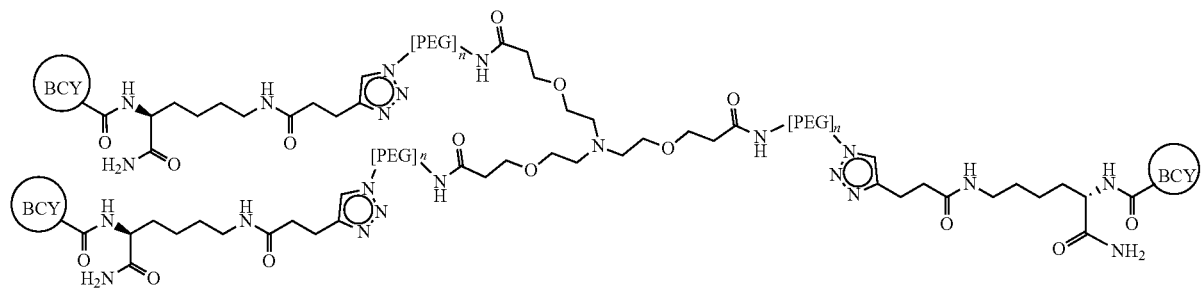

wherein BCY represents a peptide ligand of SEQ ID NO: 43 comprising a molecular scaffold which is TATA and the peptide ligand comprises A-(SEQ ID NO: 1)-A-[K(PYA)] n represents 10 (BCY18122) or 23 (BCY18118).

10. The multimeric binding complex according to claim 7 wherein m represents 4 and CHM is a motif of formula (C):

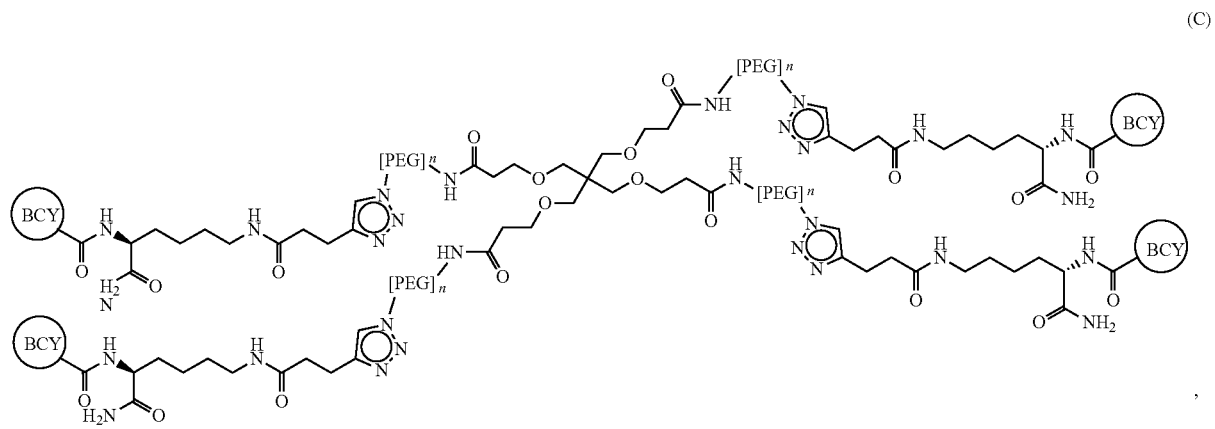

(C)

wherein BCY represents a bicyclic peptide ligand according to claim 1 and n represents 1 to 50, optionally wherein the multimeric binding complex is BCY18120 and BCY18121:

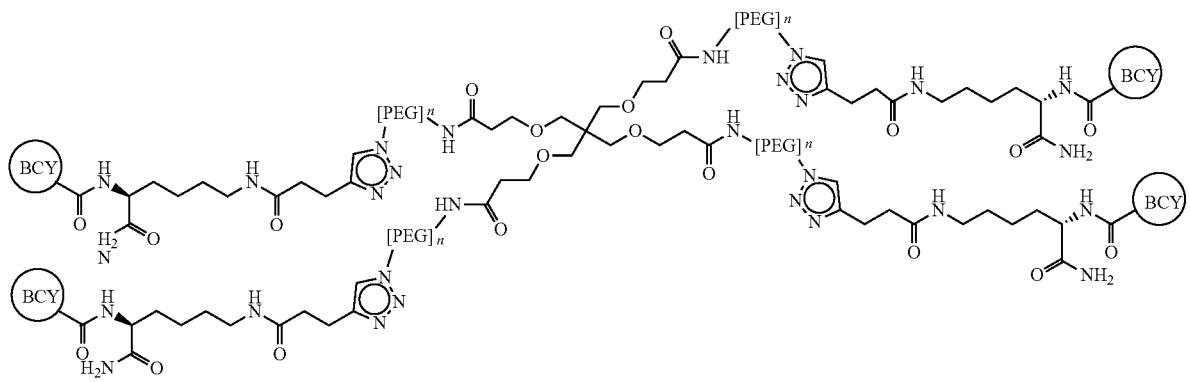

wherein BCY represents a peptide ligand of SEQ ID NO: 43 comprising a molecular scaffold which is TATA and the peptide ligand comprises A-(SEQ ID NO: 1)-A-[K(PYA)] and n represents 10 (BCY18121) or 23 (BCY18120).

11. A method of preventing, suppressing or treating a disease or disorder mediated by TREM2, comprising administering the peptide ligand according to claim 1.

12. The method of claim 11, wherein the disease or disorder mediated by TREM2 is selected from dementia, frontotemporal dementia, Alzheimer's disease, Nasu-Hakola disease, and multiple sclerosis.

* * * * *

SEQUENCE LISTING

```
<160> NUMBER OF SEQ ID NOS: 102

<210> SEQ ID NO 1
<211> LENGTH: 12
<212> TYPE: PRT
<213> ORGANISM: Artificial
<220> FEATURE:
<223> OTHER INFORMATION: Synthetic Peptide

<400> SEQUENCE: 1

Cys Ser Glu Tyr Cys Phe Trp Pro Phe Tyr His Cys
1               5                   10

<210> SEQ ID NO 2
<211> LENGTH: 12
<212> TYPE: PRT
<213> ORGANISM: Artificial
<220> FEATURE:
<223> OTHER INFORMATION: Synthetic Peptide

<400> SEQUENCE: 2

Cys Ser Glu Tyr Cys Phe Trp Pro Phe Tyr Ser Cys
1               5                   10

<210> SEQ ID NO 3
<211> LENGTH: 12
<212> TYPE: PRT
<213> ORGANISM: Artificial
<220> FEATURE:
<223> OTHER INFORMATION: Synthetic Peptide

<400> SEQUENCE: 3

Cys Ser Glu Tyr Cys Phe Trp Pro Phe Tyr Pro Cys
1               5                   10

<210> SEQ ID NO 4
<211> LENGTH: 12
<212> TYPE: PRT
<213> ORGANISM: Artificial
<220> FEATURE:
<223> OTHER INFORMATION: Synthetic Peptide

<400> SEQUENCE: 4

Cys Ser Glu Tyr Cys Phe Trp Pro Phe Trp Asn Cys
1               5                   10

<210> SEQ ID NO 5
<211> LENGTH: 12
<212> TYPE: PRT
<213> ORGANISM: Artificial
<220> FEATURE:
```

```
<223> OTHER INFORMATION: Synthetic Peptide

<400> SEQUENCE: 5

Cys Ser Glu Tyr Cys Phe Trp Pro Leu Trp Gly Cys
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic Peptide

<400> SEQUENCE: 6

Cys Ser Ala Gln Cys Ile Arg Pro Phe Tyr His Cys
1               5                   10

<210> SEQ ID NO 7
<211> LENGTH: 12
<212> TYPE: PRT
<213> ORGANISM: Artificial
<220> FEATURE:
<223> OTHER INFORMATION: Synthetic Peptide

<400> SEQUENCE: 7

Cys Ser Glu Tyr Cys Phe Trp Pro Leu Phe Gly Cys
1               5                   10

<210> SEQ ID NO 8
<211> LENGTH: 12
<212> TYPE: PRT
<213> ORGANISM: Artificial
<220> FEATURE:
<223> OTHER INFORMATION: Synthetic Peptide

<400> SEQUENCE: 8

Cys Ser Tyr Tyr Cys Phe Trp Pro Phe Gln Ser Cys
1               5                   10

<210> SEQ ID NO 9
<211> LENGTH: 12
<212> TYPE: PRT
<213> ORGANISM: Artificial
<220> FEATURE:
<223> OTHER INFORMATION: Synthetic Peptide

<400> SEQUENCE: 9

Cys Ser Tyr Tyr Cys Phe Trp Pro Phe Gln Tyr Cys
1               5                   10

<210> SEQ ID NO 10
<211> LENGTH: 12
<212> TYPE: PRT
<213> ORGANISM: Artificial
<220> FEATURE:
<223> OTHER INFORMATION: Synthetic Peptide

<400> SEQUENCE: 10

Cys Thr Ser Tyr Cys Phe Trp Pro Phe Tyr Gln Cys
1               5                   10

<210> SEQ ID NO 11
<211> LENGTH: 12
<212> TYPE: PRT
<213> ORGANISM: Artificial
<220> FEATURE:
<223> OTHER INFORMATION: Synthetic Peptide
```

<400> SEQUENCE: 11

Cys Thr Asn Tyr Cys Phe Trp Pro Phe Trp Ser Cys
1               5                   10

<210> SEQ ID NO 12
<211> LENGTH: 12
<212> TYPE: PRT
<213> ORGANISM: Artificial
<220> FEATURE:
<223> OTHER INFORMATION: Synthetic Peptide

<400> SEQUENCE: 12

Cys Ser Asn Tyr Cys Phe Trp Pro Phe Trp Gln Cys
1               5                   10

<210> SEQ ID NO 13
<211> LENGTH: 12
<212> TYPE: PRT
<213> ORGANISM: Artificial
<220> FEATURE:
<223> OTHER INFORMATION: Synthetic Peptide

<400> SEQUENCE: 13

Cys Ser Glu Tyr Cys Phe Trp Pro Phe Gln Trp Cys
1               5                   10

<210> SEQ ID NO 14
<211> LENGTH: 12
<212> TYPE: PRT
<213> ORGANISM: Artificial
<220> FEATURE:
<223> OTHER INFORMATION: Synthetic Peptide

<400> SEQUENCE: 14

Cys Ser Asn Tyr Cys Phe Trp Pro Phe Phe Gln Cys
1               5                   10

<210> SEQ ID NO 15
<211> LENGTH: 12
<212> TYPE: PRT
<213> ORGANISM: Artificial
<220> FEATURE:
<223> OTHER INFORMATION: Synthetic Peptide

<400> SEQUENCE: 15

Cys Ser Glu Tyr Cys Phe Trp Pro Phe Phe Leu Cys
1               5                   10

<210> SEQ ID NO 16
<211> LENGTH: 12
<212> TYPE: PRT
<213> ORGANISM: Artificial
<220> FEATURE:
<223> OTHER INFORMATION: Synthetic Peptide

<400> SEQUENCE: 16

Cys Ser Glu Tyr Cys Phe Trp Pro Phe Tyr Leu Cys
1               5                   10

<210> SEQ ID NO 17
<211> LENGTH: 12
<212> TYPE: PRT
<213> ORGANISM: Artificial
<220> FEATURE:
<223> OTHER INFORMATION: Synthetic Peptide

```
<400> SEQUENCE: 17

Cys Ser Glu Tyr Cys Phe Trp Pro Phe Trp Gln Cys
1               5                   10

<210> SEQ ID NO 18
<211> LENGTH: 12
<212> TYPE: PRT
<213> ORGANISM: Artificial
<220> FEATURE:
<223> OTHER INFORMATION: Synthetic Peptide

<400> SEQUENCE: 18

Cys Thr Asn Tyr Cys Phe Trp Pro Phe Gln Tyr Cys
1               5                   10

<210> SEQ ID NO 19
<211> LENGTH: 12
<212> TYPE: PRT
<213> ORGANISM: Artificial
<220> FEATURE:
<223> OTHER INFORMATION: Synthetic Peptide

<400> SEQUENCE: 19

Cys Thr Asn Tyr Cys Phe Trp Pro Phe Gln Ser Cys
1               5                   10

<210> SEQ ID NO 20
<211> LENGTH: 12
<212> TYPE: PRT
<213> ORGANISM: Artificial
<220> FEATURE:
<223> OTHER INFORMATION: Synthetic Peptide

<400> SEQUENCE: 20

Cys Thr Asn Tyr Cys Phe Trp Pro Phe Tyr Ser Cys
1               5                   10

<210> SEQ ID NO 21
<211> LENGTH: 12
<212> TYPE: PRT
<213> ORGANISM: Artificial
<220> FEATURE:
<223> OTHER INFORMATION: Synthetic Peptide

<400> SEQUENCE: 21

Cys Thr Asn Tyr Cys Phe Trp Pro Phe Tyr Leu Cys
1               5                   10

<210> SEQ ID NO 22
<211> LENGTH: 12
<212> TYPE: PRT
<213> ORGANISM: Artificial
<220> FEATURE:
<223> OTHER INFORMATION: Synthetic Peptide

<400> SEQUENCE: 22

Cys Thr Asn Tyr Cys Phe Trp Pro Phe Ala Val Cys
1               5                   10

<210> SEQ ID NO 23
<211> LENGTH: 12
<212> TYPE: PRT
<213> ORGANISM: Artificial
<220> FEATURE:
<223> OTHER INFORMATION: Synthetic Peptide

<400> SEQUENCE: 23
```

```
Cys Ser Glu Tyr Cys Phe Trp Pro Phe Gln Tyr Cys
1               5                   10

<210> SEQ ID NO 24
<211> LENGTH: 12
<212> TYPE: PRT
<213> ORGANISM: Artificial
<220> FEATURE:
<223> OTHER INFORMATION: Synthetic Peptide

<400> SEQUENCE: 24

Cys Ala Glu Tyr Cys Phe Trp Pro Phe Tyr His Cys
1               5                   10

<210> SEQ ID NO 25
<211> LENGTH: 12
<212> TYPE: PRT
<213> ORGANISM: Artificial
<220> FEATURE:
<223> OTHER INFORMATION: Synthetic Peptide

<400> SEQUENCE: 25

Cys Ser Ala Tyr Cys Phe Trp Pro Phe Tyr His Cys
1               5                   10

<210> SEQ ID NO 26
<211> LENGTH: 12
<212> TYPE: PRT
<213> ORGANISM: Artificial
<220> FEATURE:
<223> OTHER INFORMATION: Synthetic Peptide

<400> SEQUENCE: 26

Cys Ser Glu Tyr Cys Phe Trp Ala Phe Tyr His Cys
1               5                   10

<210> SEQ ID NO 27
<211> LENGTH: 12
<212> TYPE: PRT
<213> ORGANISM: Artificial
<220> FEATURE:
<223> OTHER INFORMATION: Synthetic Peptide

<400> SEQUENCE: 27

Cys Ser Glu Tyr Cys Phe Trp Pro Phe Ala His Cys
1               5                   10

<210> SEQ ID NO 28
<211> LENGTH: 12
<212> TYPE: PRT
<213> ORGANISM: Artificial
<220> FEATURE:
<223> OTHER INFORMATION: Synthetic Peptide

<400> SEQUENCE: 28

Cys Ser Glu Tyr Cys Phe Trp Pro Phe Tyr Ala Cys
1               5                   10

<210> SEQ ID NO 29
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
```

<223> OTHER INFORMATION: Xaa is 2,6-DiMeTyr

<400> SEQUENCE: 29

Cys Ser Glu Xaa Cys Phe Trp Pro Phe Tyr Ala Cys
1               5                   10

<210> SEQ ID NO 30
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (6)..(6)
<223> OTHER INFORMATION: Xaa is 4MePhe

<400> SEQUENCE: 30

Cys Ser Glu Tyr Cys Xaa Trp Pro Phe Tyr Ala Cys
1               5                   10

<210> SEQ ID NO 31
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (6)..(6)
<223> OTHER INFORMATION: Xaa is HPhe

<400> SEQUENCE: 31

Cys Ser Glu Tyr Cys Xaa Trp Pro Phe Tyr Ala Cys
1               5                   10

<210> SEQ ID NO 32
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is 1Nal

<400> SEQUENCE: 32

Cys Ser Glu Tyr Cys Phe Xaa Pro Phe Tyr Ala Cys
1               5                   10

<210> SEQ ID NO 33
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is 2Nal

<400> SEQUENCE: 33

Cys Ser Glu Tyr Cys Phe Xaa Pro Phe Tyr Ala Cys
1               5                   10

<210> SEQ ID NO 34
<211> LENGTH: 12
<212> TYPE: PRT

```
<213> ORGANISM: Artificial
<220> FEATURE:
<223> OTHER INFORMATION: Synthetic Peptide
<220> FEATURE:
<221> NAME/KEY: Xaa
<222> LOCATION: (8)..(8)
<223> OTHER INFORMATION: Xaa is NMeAla

<400> SEQUENCE: 34

Cys Ser Glu Tyr Cys Phe Trp Xaa Phe Tyr Ala Cys
1               5                   10

<210> SEQ ID NO 35
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is HPhe

<400> SEQUENCE: 35

Cys Ser Glu Tyr Cys Phe Trp Pro Xaa Tyr Ala Cys
1               5                   10

<210> SEQ ID NO 36
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is 4MePhe

<400> SEQUENCE: 36

Cys Ser Glu Tyr Cys Phe Trp Pro Xaa Tyr Ala Cys
1               5                   10

<210> SEQ ID NO 37
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is 1Nal

<400> SEQUENCE: 37

Cys Ser Glu Tyr Cys Phe Xaa Pro Phe Tyr His Cys
1               5                   10

<210> SEQ ID NO 38
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is HPhe

<400> SEQUENCE: 38

Cys Ser Glu Tyr Cys Phe Trp Pro Xaa Tyr His Cys
```

<210> SEQ ID NO 39
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
<222> LOCATION: (9)..(9)
<223> OTHER INFORMATION: Xaa is HPhe

<400> SEQUENCE: 39

Cys Ser Glu Tyr Cys Phe Xaa Pro Xaa Tyr His Cys
1               5                   10

<210> SEQ ID NO 40
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is 1Nal

<400> SEQUENCE: 40

Cys Ser Glu Tyr Cys Phe Trp Pro Xaa Tyr His Cys
1               5                   10

<210> SEQ ID NO 41
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (8)..(8)
<223> OTHER INFORMATION: Xaa is Aib

<400> SEQUENCE: 41

Cys Ser Glu Tyr Cys Phe Trp Xaa Phe Tyr His Cys
1               5                   10

<210> SEQ ID NO 42
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is 6ClTrp

<400> SEQUENCE: 42

Cys Ser Glu Tyr Cys Phe Xaa Pro Phe Tyr His Cys
1               5                   10

<210> SEQ ID NO 43
<211> LENGTH: 12
<212> TYPE: PRT
<213> ORGANISM: Artificial

```
<220> FEATURE:
<223> OTHER INFORMATION: Synthetic Peptide
<220> FEATURE:
<221> NAME/KEY: Xaa
<222> LOCATION: (2)..(4)
<223> OTHER INFORMATION: Xaa represents selected amino acids or non-
      natural amino acids
<220> FEATURE:
<221> NAME/KEY: Xaa
<222> LOCATION: (6)..(11)
<223> OTHER INFORMATION: Xaa represents selected amino acids or non-
      natural amino acids

<400> SEQUENCE: 43

Cys Xaa Xaa Xaa Cys Xaa Xaa Xaa Xaa Xaa Xaa Cys
1               5                   10

<210> SEQ ID NO 44
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(11)
<223> OTHER INFORMATION: Xaa is any amino acid

<400> SEQUENCE: 44

Cys Ser Glu Tyr Cys Phe Trp Pro Xaa Xaa Xaa Cys
1               5                   10

<210> SEQ ID NO 45
<211> LENGTH: 12
<212> TYPE: PRT
<213> ORGANISM: Artificial
<220> FEATURE:
<223> OTHER INFORMATION: Synthetic Peptide

<400> SEQUENCE: 45

Cys Ser Glu Tyr Cys Phe Trp Pro Phe Phe Asn Cys
1               5                   10

<210> SEQ ID NO 46
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is 1Nal

<400> SEQUENCE: 46

Cys Ser Glu Tyr Cys Phe Trp Pro Xaa Tyr Ala Cys
1               5                   10

<210> SEQ ID NO 47
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is DOPA

<400> SEQUENCE: 47
```

```
Cys Ser Glu Xaa Cys Phe Trp Pro Phe Tyr His Cys
1               5                   10

<210> SEQ ID NO 48
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (4)..(4)
<223> OTHER INFORMATION: Xaa is 3FTyr

<400> SEQUENCE: 48

Cys Ser Glu Xaa Cys Phe Trp Pro Phe Tyr His Cys
1               5                   10

<210> SEQ ID NO 49
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (6)..(6)
<223> OTHER INFORMATION: Xaa is 1Nal

<400> SEQUENCE: 49

Cys Ser Glu Tyr Cys Xaa Trp Pro Phe Tyr His Cys
1               5                   10

<210> SEQ ID NO 50
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (6)..(6)
<223> OTHER INFORMATION: Xaa is 4FPhe

<400> SEQUENCE: 50

Cys Ser Glu Tyr Cys Xaa Trp Pro Phe Tyr His Cys
1               5                   10

<210> SEQ ID NO 51
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (6)..(6)
<223> OTHER INFORMATION: Xaa is 2FPhe

<400> SEQUENCE: 51

Cys Ser Glu Tyr Cys Xaa Trp Pro Phe Tyr His Cys
1               5                   10

<210> SEQ ID NO 52
<211> LENGTH: 12
<212> TYPE: PRT
<213> ORGANISM: Artificial
<220> FEATURE:
<223> OTHER INFORMATION: Synthetic Peptide
<220> FEATURE:
```

```
<221> NAME/KEY: Xaa
<222> LOCATION: (6)..(6)
<223> OTHER INFORMATION: Xaa is 3FPhe

<400> SEQUENCE: 52

Cys Ser Glu Tyr Cys Xaa Trp Pro Phe Tyr His Cys
1               5                   10

<210> SEQ ID NO 53
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is Trp(Me)

<400> SEQUENCE: 53

Cys Ser Glu Tyr Cys Phe Xaa Pro Phe Tyr His Cys
1               5                   10

<210> SEQ ID NO 54
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is 6MeTrp

<400> SEQUENCE: 54

Cys Ser Glu Tyr Cys Phe Xaa Pro Phe Tyr His Cys
1               5                   10

<210> SEQ ID NO 55
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is 5FTrp

<400> SEQUENCE: 55

Cys Ser Glu Tyr Cys Phe Xaa Pro Phe Tyr His Cys
1               5                   10

<210> SEQ ID NO 56
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is 6FTrp

<400> SEQUENCE: 56

Cys Ser Glu Tyr Cys Phe Xaa Pro Phe Tyr His Cys
1               5                   10

<210> SEQ ID NO 57
```

```
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is 3MePhe

<400> SEQUENCE: 57

Cys Ser Glu Tyr Cys Phe Xaa Pro Phe Tyr His Cys
1               5                   10

<210> SEQ ID NO 58
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is 2Nal

<400> SEQUENCE: 58

Cys Ser Glu Tyr Cys Phe Xaa Pro Phe Tyr His Cys
1               5                   10

<210> SEQ ID NO 59
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is AzaTrp

<400> SEQUENCE: 59

Cys Ser Glu Tyr Cys Phe Xaa Pro Phe Tyr His Cys
1               5                   10

<210> SEQ ID NO 60
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is CF3Phe

<400> SEQUENCE: 60

Cys Ser Glu Tyr Cys Phe Xaa Pro Phe Tyr His Cys
1               5                   10

<210> SEQ ID NO 61
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is 2MePhe

<400> SEQUENCE: 61
```

```
Cys Ser Glu Tyr Cys Phe Xaa Pro Phe Tyr His Cys
1               5                   10
```

<210> SEQ ID NO 62
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (8)..(8)
<223> OTHER INFORMATION: Xaa is Pip

<400> SEQUENCE: 62

```
Cys Ser Glu Tyr Cys Phe Trp Xaa Phe Tyr His Cys
1               5                   10
```

<210> SEQ ID NO 63
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (8)..(8)
<223> OTHER INFORMATION: Xaa is 44DFP

<400> SEQUENCE: 63

```
Cys Ser Glu Tyr Cys Phe Trp Xaa Phe Tyr His Cys
1               5                   10
```

<210> SEQ ID NO 64
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (8)..(8)
<223> OTHER INFORMATION: Xaa is Aze

<400> SEQUENCE: 64

```
Cys Ser Glu Tyr Cys Phe Trp Xaa Phe Tyr His Cys
1               5                   10
```

<210> SEQ ID NO 65
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (8)..(8)
<223> OTHER INFORMATION: Xaa is Cis-HyP

<400> SEQUENCE: 65

```
Cys Ser Glu Tyr Cys Phe Trp Xaa Phe Tyr His Cys
1               5                   10
```

<210> SEQ ID NO 66
<211> LENGTH: 12
<212> TYPE: PRT
<213> ORGANISM: Artificial
<220> FEATURE:
<223> OTHER INFORMATION: Synthetic Peptide

```
<220> FEATURE:
<221> NAME/KEY: Xaa
<222> LOCATION: (9)..(9)
<223> OTHER INFORMATION: Xaa is 2MePhe

<400> SEQUENCE: 66

Cys Ser Glu Tyr Cys Phe Trp Pro Xaa Tyr His Cys
1               5                   10

<210> SEQ ID NO 67
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is 4FPhe

<400> SEQUENCE: 67

Cys Ser Glu Tyr Cys Phe Trp Pro Xaa Tyr His Cys
1               5                   10

<210> SEQ ID NO 68
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is tBuAla

<400> SEQUENCE: 68

Cys Ser Glu Tyr Cys Phe Trp Pro Xaa Tyr His Cys
1               5                   10

<210> SEQ ID NO 69
<211> LENGTH: 12
<212> TYPE: PRT
<213> ORGANISM: Artificial
<220> FEATURE:
<223> OTHER INFORMATION: Synthetic Peptide

<400> SEQUENCE: 69

Cys Ser Glu Tyr Cys Phe Trp Pro Leu Tyr His Cys
1               5                   10

<210> SEQ ID NO 70
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is 3MePhe

<400> SEQUENCE: 70

Cys Ser Glu Tyr Cys Phe Trp Pro Xaa Tyr His Cys
1               5                   10

<210> SEQ ID NO 71
<211> LENGTH: 12
<212> TYPE: PRT
<213> ORGANISM: Artificial
```

```
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is 44BPA

<400> SEQUENCE: 71

Cys Ser Glu Tyr Cys Phe Trp Pro Xaa Tyr His Cys
1               5                   10

<210> SEQ ID NO 72
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is 2Nal

<400> SEQUENCE: 72

Cys Ser Glu Tyr Cys Phe Trp Pro Xaa Tyr His Cys
1               5                   10

<210> SEQ ID NO 73
<211> LENGTH: 12
<212> TYPE: PRT
<213> ORGANISM: Artificial
<220> FEATURE:
<223> OTHER INFORMATION: Synthetic Peptide

<400> SEQUENCE: 73

Cys Ser Glu Tyr Cys Phe Trp Pro Phe Trp His Cys
1               5                   10

<210> SEQ ID NO 74
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is 4FPhe

<400> SEQUENCE: 74

Cys Ser Glu Tyr Cys Phe Trp Pro Phe Xaa His Cys
1               5                   10

<210> SEQ ID NO 75
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is 2Nal

<400> SEQUENCE: 75

Cys Ser Glu Tyr Cys Phe Trp Pro Phe Xaa His Cys
1               5                   10

<210> SEQ ID NO 76
<211> LENGTH: 12
```

<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is 3tBuTyr

<400> SEQUENCE: 76

Cys Ser Glu Tyr Cys Phe Trp Pro Phe Xaa His Cys
1               5                   10

<210> SEQ ID NO 77
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is 1Nal

<400> SEQUENCE: 77

Cys Ser Glu Tyr Cys Phe Trp Pro Phe Xaa His Cys
1               5                   10

<210> SEQ ID NO 78
<211> LENGTH: 12
<212> TYPE: PRT
<213> ORGANISM: Artificial
<220> FEATURE:
<223> OTHER INFORMATION: Synthetic Peptide

<400> SEQUENCE: 78

Cys Ser Glu Tyr Cys Phe Trp Pro Phe Tyr Asn Cys
1               5                   10

<210> SEQ ID NO 79
<211> LENGTH: 12
<212> TYPE: PRT
<213> ORGANISM: Artificial
<220> FEATURE:
<223> OTHER INFORMATION: Synthetic Peptide

<400> SEQUENCE: 79

Cys Ala Glu Tyr Cys Phe Trp Pro Phe Tyr His Cys
1               5                   10

<210> SEQ ID NO 80
<211> LENGTH: 12
<212> TYPE: PRT
<213> ORGANISM: Artificial
<220> FEATURE:
<223> OTHER INFORMATION: Synthetic Peptide

<400> SEQUENCE: 80

Cys Ser Ala Tyr Cys Phe Trp Pro Phe Tyr His Cys
1               5                   10

<210> SEQ ID NO 81
<211> LENGTH: 12
<212> TYPE: PRT
<213> ORGANISM: Artificial
<220> FEATURE:
<223> OTHER INFORMATION: Synthetic Peptide

<400> SEQUENCE: 81

```
Cys Ser Glu Tyr Cys Phe Trp Pro Phe Ala His Cys
1               5                   10
```

<210> SEQ ID NO 82
<211> LENGTH: 12
<212> TYPE: PRT
<213> ORGANISM: Artificial
<220> FEATURE:
<223> OTHER INFORMATION: Synthetic Peptide

<400> SEQUENCE: 82

```
Cys Ser Glu Tyr Cys Phe Trp Pro Phe Tyr Ala Cys
1               5                   10
```

<210> SEQ ID NO 83
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is K(PYA)

<400> SEQUENCE: 83

```
Cys Xaa Glu Tyr Cys Phe Trp Pro Phe Tyr His Cys
1               5                   10
```

<210> SEQ ID NO 84
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is K(PYA)

<400> SEQUENCE: 84

```
Cys Ser Xaa Tyr Cys Phe Trp Pro Phe Tyr His Cys
1               5                   10
```

<210> SEQ ID NO 85
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is K(PYA)

<400> SEQUENCE: 85

```
Cys Ser Glu Tyr Cys Phe Trp Pro Xaa Tyr His Cys
1               5                   10
```

<210> SEQ ID NO 86
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is K(PYA)

```
<400> SEQUENCE: 86

Cys Ser Glu Tyr Cys Phe Trp Pro Phe Xaa His Cys
1               5                   10

<210> SEQ ID NO 87
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is K(PYA)

<400> SEQUENCE: 87

Cys Ser Glu Tyr Cys Phe Trp Pro Phe Tyr Xaa Cys
1               5                   10

<210> SEQ ID NO 88
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is HPhe

<400> SEQUENCE: 88

Cys Ser Glu Tyr Cys Phe Trp Pro Xaa Gln Tyr Cys
1               5                   10

<210> SEQ ID NO 89
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is 1Nal

<400> SEQUENCE: 89

Cys Ser Glu Tyr Cys Phe Trp Pro Xaa Gln Tyr Cys
1               5                   10

<210> SEQ ID NO 90
<211> LENGTH: 12
<212> TYPE: PRT
<213> ORGANISM: Artificial
<220> FEATURE:
<223> OTHER INFORMATION: Synthetic Peptide

<400> SEQUENCE: 90

Cys Asp Glu Tyr Cys Phe Trp Pro Phe Tyr His Cys
1               5                   10

<210> SEQ ID NO 91
<211> LENGTH: 12
<212> TYPE: PRT
<213> ORGANISM: Artificial
<220> FEATURE:
<223> OTHER INFORMATION: Synthetic Peptide

<400> SEQUENCE: 91
```

Cys Glu Glu Tyr Cys Phe Trp Pro Phe Tyr His Cys
1               5                   10

<210> SEQ ID NO 92
<211> LENGTH: 12
<212> TYPE: PRT
<213> ORGANISM: Artificial
<220> FEATURE:
<223> OTHER INFORMATION: Synthetic Peptide

<400> SEQUENCE: 92

Cys Ser Glu Tyr Cys Tyr Trp Pro Phe Tyr His Cys
1               5                   10

<210> SEQ ID NO 93
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (6)..(6)
<223> OTHER INFORMATION: Xaa is 4Pal

<400> SEQUENCE: 93

Cys Ser Glu Tyr Cys Xaa Trp Pro Phe Tyr His Cys
1               5                   10

<210> SEQ ID NO 94
<211> LENGTH: 12
<212> TYPE: PRT
<213> ORGANISM: Artificial
<220> FEATURE:
<223> OTHER INFORMATION: Synthetic Peptide

<400> SEQUENCE: 94

Cys Ser Glu Tyr Cys Phe Trp Pro Tyr Tyr His Cys
1               5                   10

<210> SEQ ID NO 95
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (9)..(9)
<223> OTHER INFORMATION: Xaa is 4Pal

<400> SEQUENCE: 95

Cys Ser Glu Tyr Cys Phe Trp Pro Xaa Tyr His Cys
1               5                   10

<210> SEQ ID NO 96
<211> LENGTH: 12
<212> TYPE: PRT
<213> ORGANISM: Artificial
<220> FEATURE:
<223> OTHER INFORMATION: Synthetic Peptide

<400> SEQUENCE: 96

Cys Ser Glu Tyr Cys Phe Trp Pro Phe Asp His Cys
1               5                   10

<210> SEQ ID NO 97

```
<211> LENGTH: 12
<212> TYPE: PRT
<213> ORGANISM: Artificial
<220> FEATURE:
<223> OTHER INFORMATION: Synthetic Peptide

<400> SEQUENCE: 97

Cys Ser Glu Tyr Cys Phe Trp Pro Phe Glu His Cys
1               5                   10

<210> SEQ ID NO 98
<211> LENGTH: 12
<212> TYPE: PRT
<213> ORGANISM: Artificial
<220> FEATURE:
<223> OTHER INFORMATION: Synthetic Peptide

<400> SEQUENCE: 98

Cys Ser Glu Tyr Cys Phe Trp Pro Phe Tyr Gln Cys
1               5                   10

<210> SEQ ID NO 99
<211> LENGTH: 12
<212> TYPE: PRT
<213> ORGANISM: Artificial
<220> FEATURE:
<223> OTHER INFORMATION: Synthetic Peptide

<400> SEQUENCE: 99

Cys Ser Glu Tyr Cys Phe Trp Pro Phe Tyr Asp Cys
1               5                   10

<210> SEQ ID NO 100
<211> LENGTH: 12
<212> TYPE: PRT
<213> ORGANISM: Artificial
<220> FEATURE:
<223> OTHER INFORMATION: Synthetic Peptide

<400> SEQUENCE: 100

Cys Ser Glu Tyr Cys Phe Trp Pro Phe Tyr Glu Cys
1               5                   10

<210> SEQ ID NO 101
<211> LENGTH: 12
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (11)..(11)
<223> OTHER INFORMATION: Xaa is HArg

<400> SEQUENCE: 101

Cys Ser Glu Tyr Cys Phe Trp Pro Phe Tyr Xaa Cys
1               5                   10

<210> SEQ ID NO 102
<211> LENGTH: 12
```

```
<212> TYPE: PRT
<213> ORGANISM: Artificial
<220> FEATURE:
<223> OTHER INFORMATION: Synthetic Peptide

<400> SEQUENCE: 102

Cys Ser Glu Tyr Cys Phe Trp Pro Phe Tyr Phe Cys
1               5                   10
```